United States Patent
Kim et al.

(10) Patent No.: US 12,251,471 B2
(45) Date of Patent: Mar. 18, 2025

(54) INHALABLE THERAPEUTICS

(71) Applicant: Oregon State University, Corvallis, OR (US)

(72) Inventors: Jeonghwan Kim, Corvallis, OR (US); Gaurav Sahay, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 17/872,830

(22) Filed: Jul. 25, 2022

(65) Prior Publication Data

US 2023/0043677 A1 Feb. 9, 2023

Related U.S. Application Data

(60) Provisional application No. 63/225,766, filed on Jul. 26, 2021.

(51) Int. Cl.
*A61K 9/1272* (2025.01)
*A61K 9/00* (2006.01)
*A61K 31/7105* (2006.01)

(52) U.S. Cl.
CPC .......... *A61K 9/1272* (2013.01); *A61K 9/0078* (2013.01); *A61K 31/7105* (2013.01)

(58) Field of Classification Search
CPC . A61K 9/1272; A61K 9/0078; A61K 31/7105
See application file for complete search history.

(56) References Cited

U.S. PATENT DOCUMENTS 9,867,888 B2 * 1/2018 Benenato ............. C07D 233/72
2020/0129445 A1 * 4/2020 Patel ..................... C12N 15/113

FOREIGN PATENT DOCUMENTS

| AU | 2020322014 | 2/2022 | |
| WO | WO 2015/164674 | 10/2015 | |
| WO | WO-2020056304 A1 * | 3/2020 | ......... A61K 31/7105 |
| WO | WO-2021046265 A1 * | 3/2021 | ........... A61K 31/573 |

OTHER PUBLICATIONS

Nof, "Ionizable Cationic Lipids", retrieved 2024 from https://www.nofamerica.com/store/drug-delivery-products/phospholipids-and-lipids-for-lnp-and-liposome/1-ionizable-and-cationic-lipids.html (Year: 2024).*

Millipore Sigma, "Phosphate Buffered Saline (PBS)", retrieved 2024 from https://www.sigmaaldrich.com/US/en/products/chemistry-and-biochemicals/biochemicals/biological-buffers/phosphate-buffer-saline-pbs (Year: 2024).*

(Continued)

*Primary Examiner* — Benjamin J Packard
*Assistant Examiner* — Joshua A Atkinson
(74) *Attorney, Agent, or Firm* — Klarquist Sparkman, LLP

(57) ABSTRACT

Disclosed herein are embodiments of a nanoparticle composition suitable for delivering a therapeutic agent to a subject by nebulization. The nanoparticle comprises an ionizable lipid, cholesterol or a derivative thereof, a structural lipid, and a PEG lipid. The nanoparticle may partially or completely encapsulate a therapeutic agent, and may be nebulized for administration, such as by inhalation. In some embodiments, the therapeutic agent is mRNA.

17 Claims, 31 Drawing Sheets

PEG Lipid
 Ionizable Lipid
 Structural Lipid
 Cholesterol
 Messenger RNA

(56) References Cited

OTHER PUBLICATIONS

Vencken et al, "Nebulised lipid-polymer hybrid nanoparticles for the delivery of a therapeutic anti-inflammatory microRNA to bronchial epithelial cells", ERJ Open Res., 2019, 5: 00161-2018, pp. 1-11 (Year: 2019).*

Zhang et al, "Aerosolizable Lipid Nanoparticles for Pulmonary Delivery of mRNA through Design of Experiments", Pharmaceutics, 2020, 12(11) 1042, pp. 1-16 (Year: 2020).*

Chakraborty et al., "How cholesterol stiffens unsaturated lipid membranes," *Proceedings of the National Academy of Sciences (PNAS)* 117(36):21896-21905, 2020.

Eygeris et al., "Deconvoluting Lipid Nanoparticle Structure for Messenger RNA Delivery," *Nano Letters* 20:4543-4549, 2020.

Herrera et al., "Illuminating endosomal escape of polymorphic lipid nanoparticles that boost mRNA delivery," *Biomaterials Science* 9:4289-4300, 2021.

Patel et al., "Naturally-occurring cholesterol analogues in lipid nanoparticles induce polymorphic shape and enhance intracellular delivery of mRNA," *Nature Communications* 11(1):983 (pp. 1-13), 2020.

Paunovska et al., "Nanoparticles Containing Oxidized Cholesterol Deliver mRNA to the Liver Micorenvironment at Clinically Relevant Doses," *Advanced Materials* 31:4807748 (pp. 1-7), 2019.

* cited by examiner

INHALABLE THERAPEUTICS

CROSS REFERENCE TO RELATED APPLICATION

This application claims the benefit of the earlier filing date of U.S. provisional patent application No. 63/225,766, filed on Jul. 26, 2021, which is incorporated herein by reference in its entirety.

ACKNOWLEDGMENT OF GOVERNMENT SUPPORT

This invention was made with government support under Grant No. R01 HL146736, awarded by the National Institutes of Health. The government has certain rights in the invention.

FIELD

Disclosed herein are novel nanoparticle compositions suitable for delivering therapeutic agents to a subject, formulations comprising the nanoparticles, and methods for making and using the nanoparticles and formulations.

BACKGROUND

Pulmonary gene therapy has gained significant interest as a modality to cure lung diseases, including inherited diseases and cancers. Especially, genetic disorders, such as cystic fibrosis (CF) and α1-antitrypsin deficiency, could be treated by gene therapy that repairs mutations or provides normal protein expression. Among various gene therapies, messenger RNA (mRNA) therapy aims to produce proteins to restore the proteins' functions and alleviate symptoms. Previous proof-of-principle studies demonstrated the feasibility of mRNA therapy for treating lung diseases. For instance, CFTR mRNA treatment restored the chloride ion efflux in the nasal epithelium of CFTR-deficient mice. However, despite encouraging results in preclinical studies, effective mRNA treatment for pulmonary diseases remains challenging primarily due to insufficient delivery of mRNA therapeutics.

SUMMARY

Disclosed herein are embodiments of a nanoparticle suitable for encapsulating a therapeutic agent, such as a mRNA. The nanoparticle also may be suitable for nebulization and/or delivering the therapeutic agent by inhalation. In some embodiments, the nanoparticle comprises from 30% to 65% of an ionizable lipid, from 30% to 60% of a cholesterol derivative, from 5% to 20% of a structural lipid, and from 1.5% to 12.5% of a PEG lipid, in amounts relative to each other. In some embodiments, the nanoparticle comprises from 45% to 55% of the ionizable lipid, from 37% to 40% of the cholesterol derivative, from 9% to 10% of the structural lipid, from 1.5% to 7.5% of the PEG lipid, or a combination thereof. And/or in some embodiments, the nanoparticle has a nanoparticle size of from greater than zero to 500 nm.

In certain embodiments, the ionizable lipid is DLin-MC3-DMA, the cholesterol derivative is β-sitosterol, the structural lipid is 1,2-distearoyl-sn-glycero-3-phosphocholine (DSPC), the PEG lipid is 1,2-dimyristoyl-rac-glycerol-methoxy(poly(ethylene glycol)-2000 (DMG-PEG$_{2K}$), or a combination thereof.

Also disclosed herein is a formulation comprising the disclosed nanoparticle. The formulation may comprise a therapeutic agent, such as a nucleic acid, encapsulated within the nanoparticle. The nucleic acid may be an mRNA. Additionally, or alternatively, the formulation may further comprise a carrier selected from a balanced salt solution or an isotonic saline.

A method for administering the formulation to a subject also is disclosed herein. The method may comprise administering the formulation to the subject by inhalation. In some embodiments, the method comprises nebulizing the formulation and administering the nebulized formulation to the subject, such as administering the nebulized formulation to the subject's lungs.

The foregoing and other objects, features, and advantages of the invention will become more apparent from the following detailed description, which proceeds with reference to the accompanying figures.

BRIEF DESCRIPTION OF THE DRAWINGS

FIG. 1 is a schematic representation of an exemplary mRNA-loaded LNP, illustrating how the ionizable lipid, cholesterol, structural lipid, and PEG lipid form a substantially spherical nanoparticle, encapsulating mRNA inside.

FIG. 2 is a schematic diagram of an exemplary nebulization process of an mRNA-loaded LNP, and illustrating the volume mean diameter (VMD) of the LNP.

FIG. 3 is a graph of intensity versus particle size, illustrating the size change of an exemplary Onpattro® LNP formulation during nebulization.

FIG. 4 is a graph of size and polydispersity index (PdI) versus percentage of PEG lipid, illustrating the size and polydispersity index of various LNPs with different amounts of PEG lipid before nebulization.

FIG. 5 is a graph of size and polydispersity index (PdI) versus percentage of PEG lipid, illustrating the size and polydispersity index of various LNPs with different amounts of PEG lipid after nebulization.

FIG. 6 is a graph of mRNA encapsulation versus percentage of PEG lipid, illustrating the mRNA encapsulation of various LNPs with different amounts of PEG lipid before nebulization.

FIG. 7 is a graph of cell viability versus percentage of PEG lipid, illustrating the viability of HeLa cells when exposed to various LNP-Chol before nebulization with different amounts of PEG lipid at 50 ng mRNA per well for 24 hours.

FIG. 8 is a graph of normalized luciferase expression versus percentage of PEG lipid, illustrating the effect on luciferase expression in HeLa cells of various LNP-Chol before nebulization at 50 ng mRNA per well for 24 hours.

FIG. 9 is a graph of fold change in luciferase expression versus cell line tested, illustrating the different effects of LNPs made with cholesterol (LNP-Chol/1.5) and (β-sitosterol (LNP-Sito/1.5) on luciferase expression in various cell lines.

FIG. 10 is a graph of size and polydispersity index versus percentage of PEG lipid, illustrating the different sizes and polydispersities of LNP-Chol and LNP-Sito containing various amounts of PEG lipid before nebulization.

FIG. 11 is a graph of mRNA encapsulation versus percentage of PEG lipid, illustrating the percentage of mRNA encapsulation of LNP-Chol and LNP-Sito containing various amounts of PEG lipid before nebulization.

FIG. 12 is a graph of size and polydispersity index versus percentage of PEG lipid, illustrating the different sizes and polydispersities of LNP-Chol and LNP-Sito containing various amounts of PEG lipid after nebulization.

Figure 21:
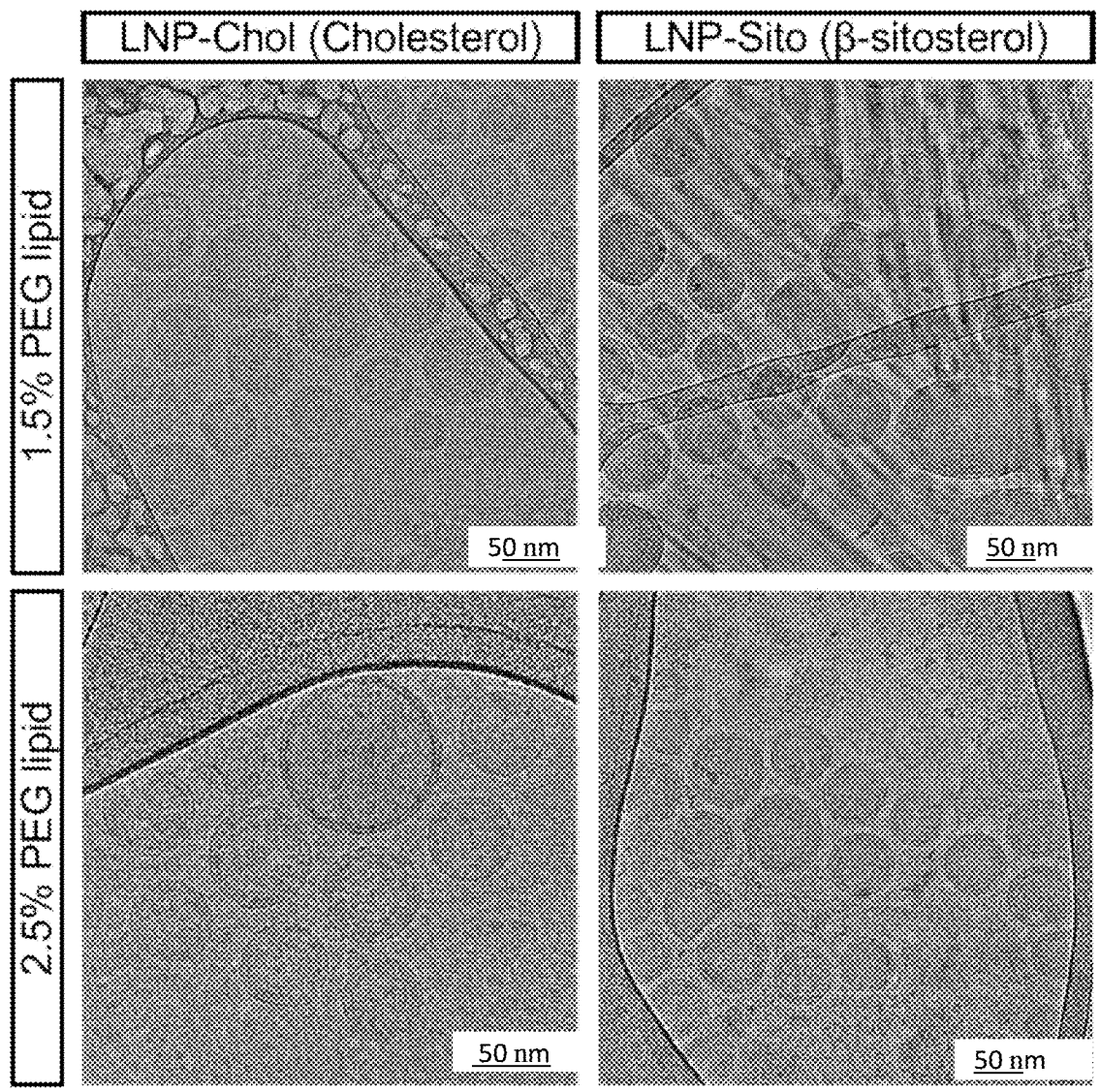

FIG. 21 provides digital images of cryogenic transmission electron microscopy (cryoTEM) imaging of LNP-Chol (left) and LNP-Sito (right) containing varying amounts of PEG lipids.

Figure 22:
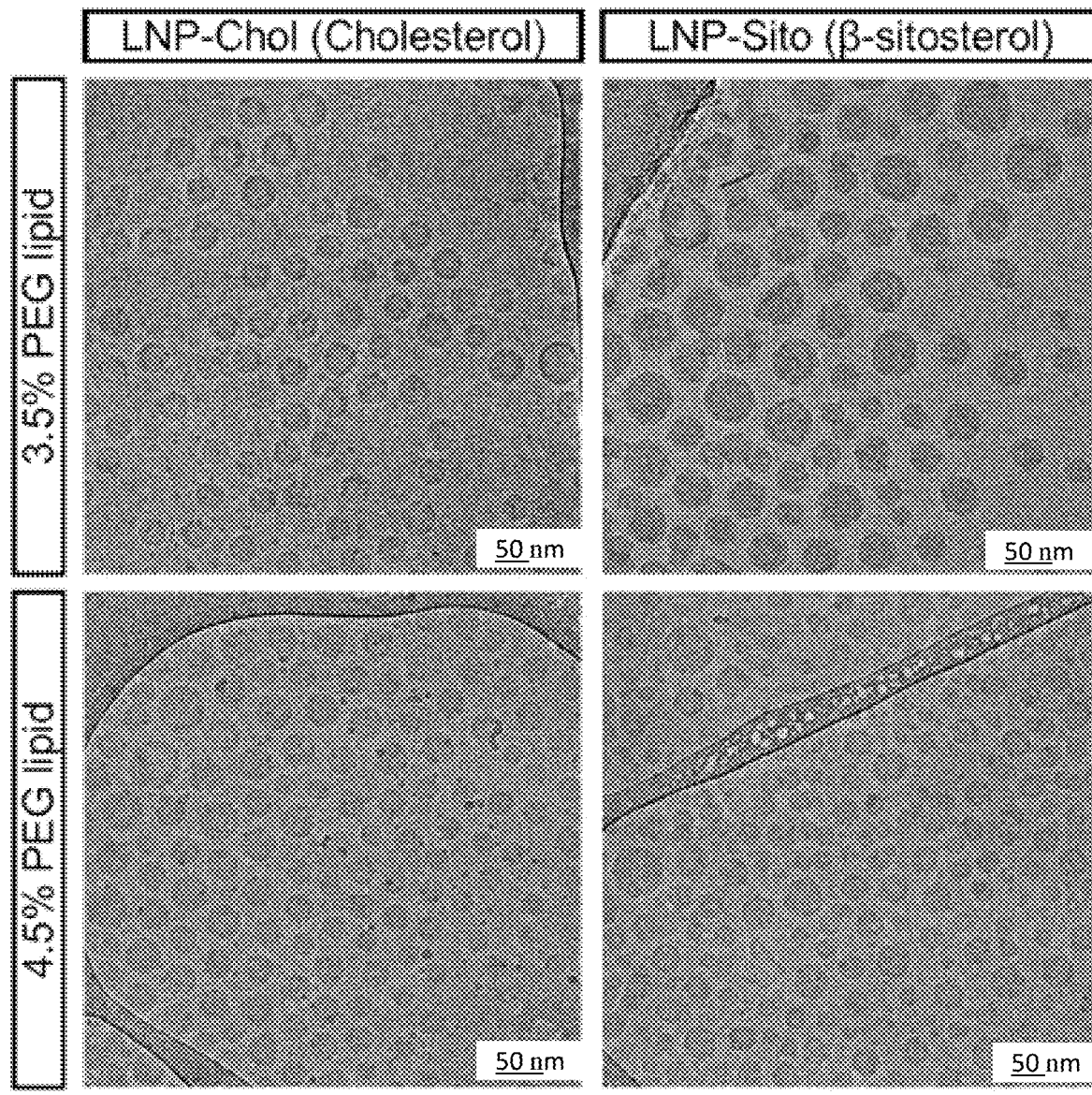

FIG. 22 provides additional digital images of cryogenic transmission electron microscopy (cryoTEM) imaging of LNP-Chol (left) and LNP-Sito (right) containing varying amounts of PEG lipids.

Figure 23:
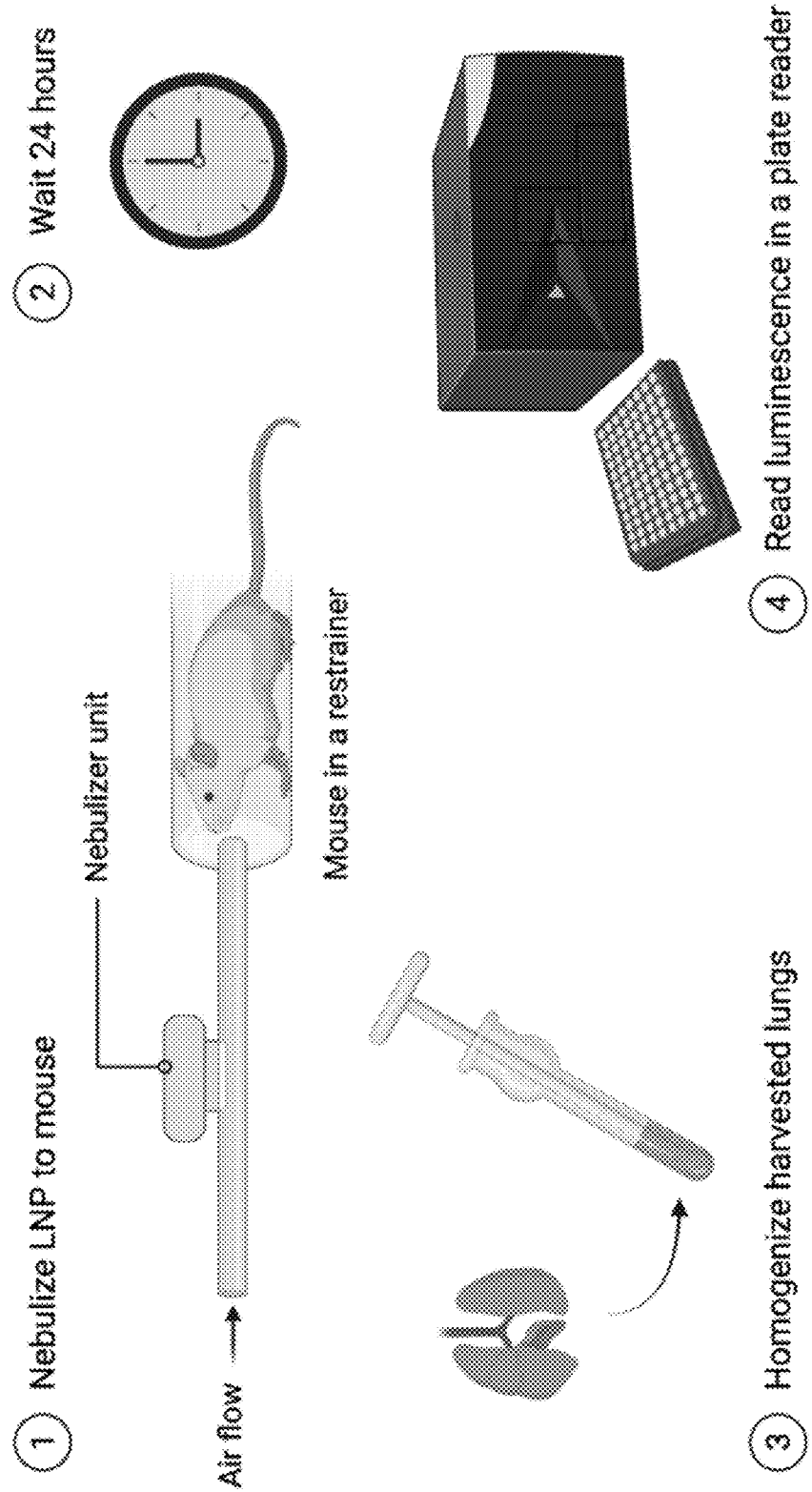

FIG. 23 is a schematic diagram, illustrating the in vivo mRNA transfection assay after LNP inhalation.

Figure 24:
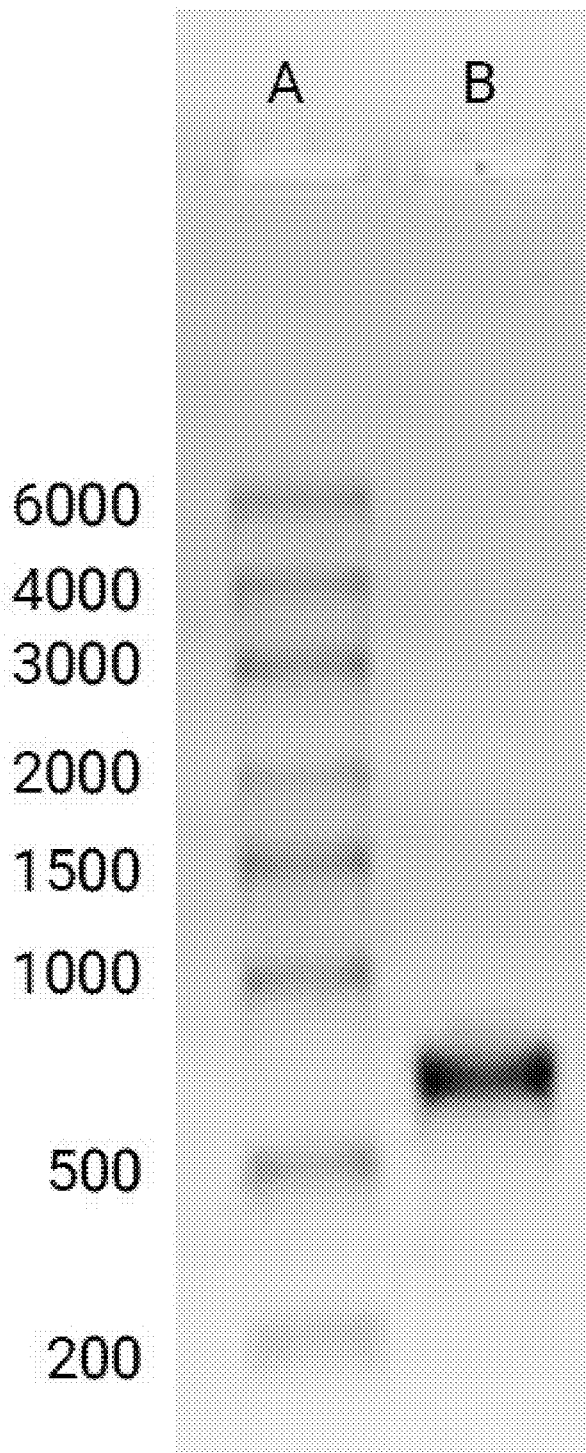

FIG. 24 is a digital image providing the results from analyzing Nluc mRNA on 1.5% formaldehyde-agrose gel electrophoresis, and illustrating that the Nluc mRNA has a size of about 800 bases (labeled B), when compared to the RNA ladder (labeled A).

Figure 25:
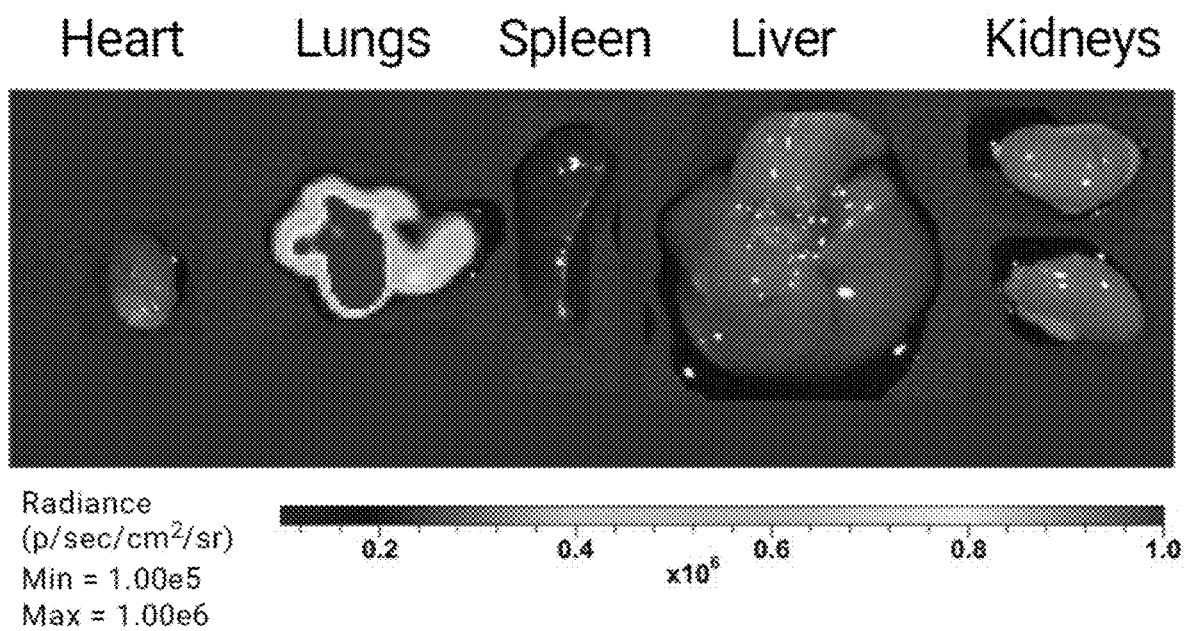

FIG. 25 is a digital image providing a bioluminescent image of isolated organs showing a localized luciferase expression in the lungs, and illustrating selective lung transfection after LNP inhalation.

Figure 26:
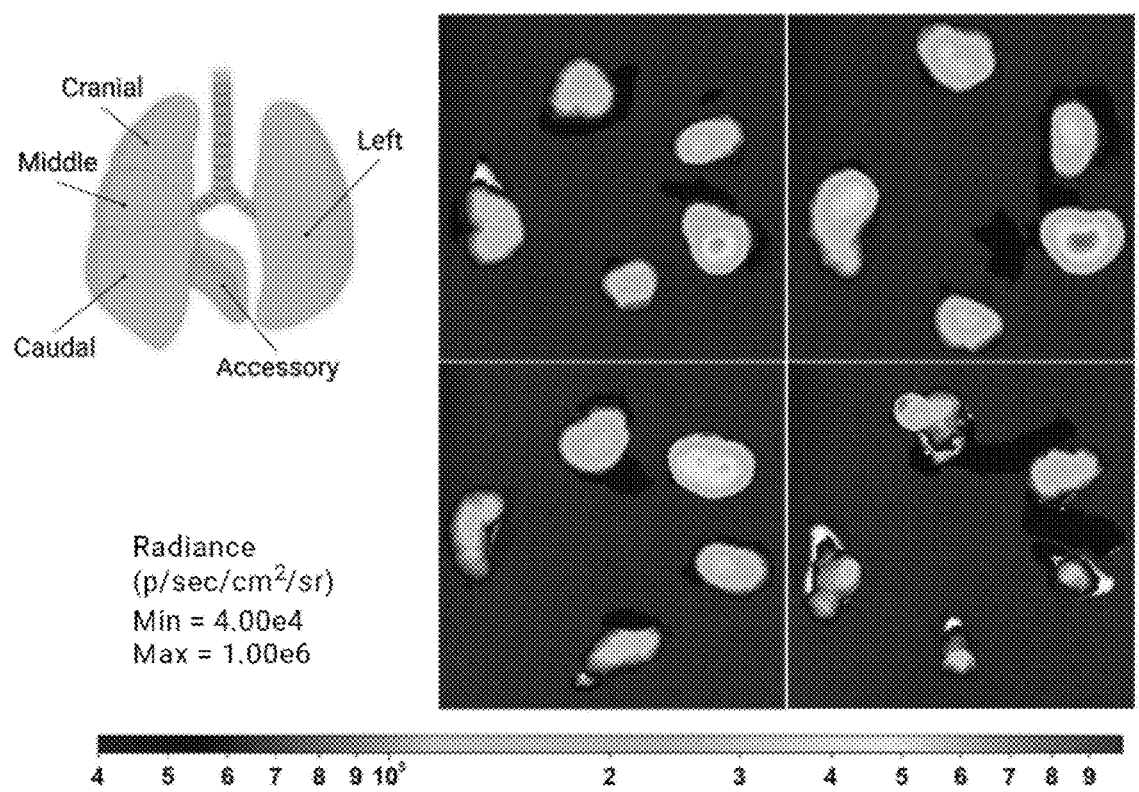

FIG. 26 provides a schematic diagram of mouse lung anatomy showing five lung lobes (left), and also provides ex vivo bioluminescent images of mouse lung lobes 24 hours after LNP inhalation, illustrating that luciferase expression was detected in all five lung lobes.

Figure 27:
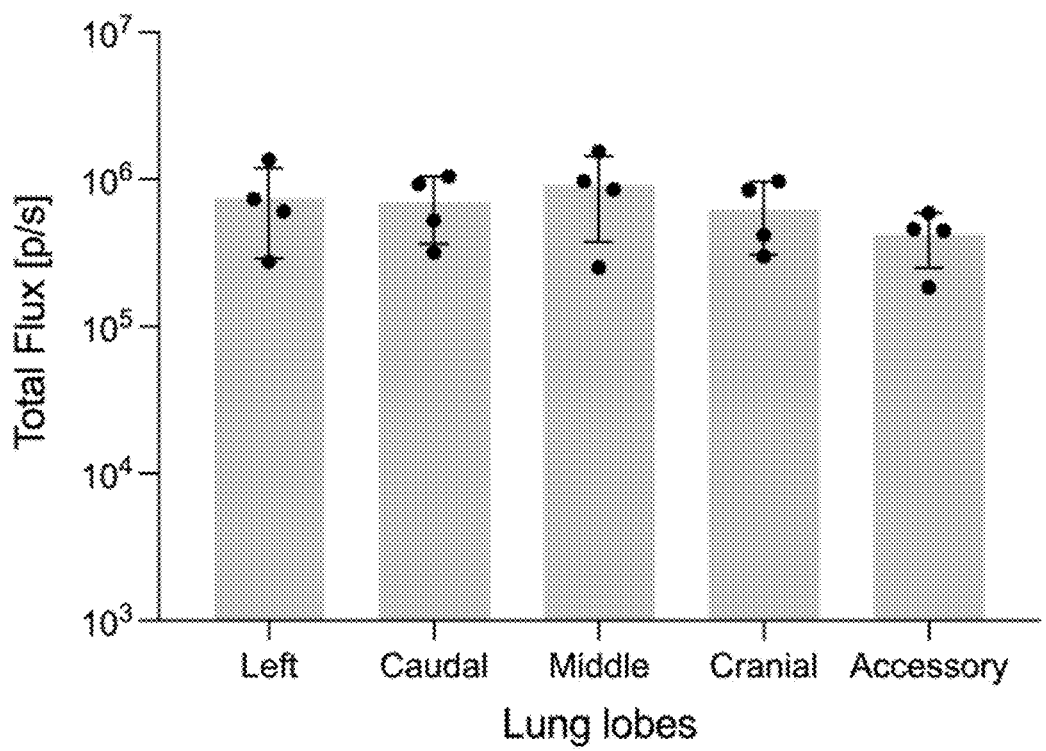

FIG. 27 is a graph of total flux versus lung lobes, illustrating the amount of total flux in individual lung lobes harvested from BALB/c mouse at 24 hours after LNP-Sito/1.5 inhalation at a dose of 100 μg mRNA.

Figure 28:
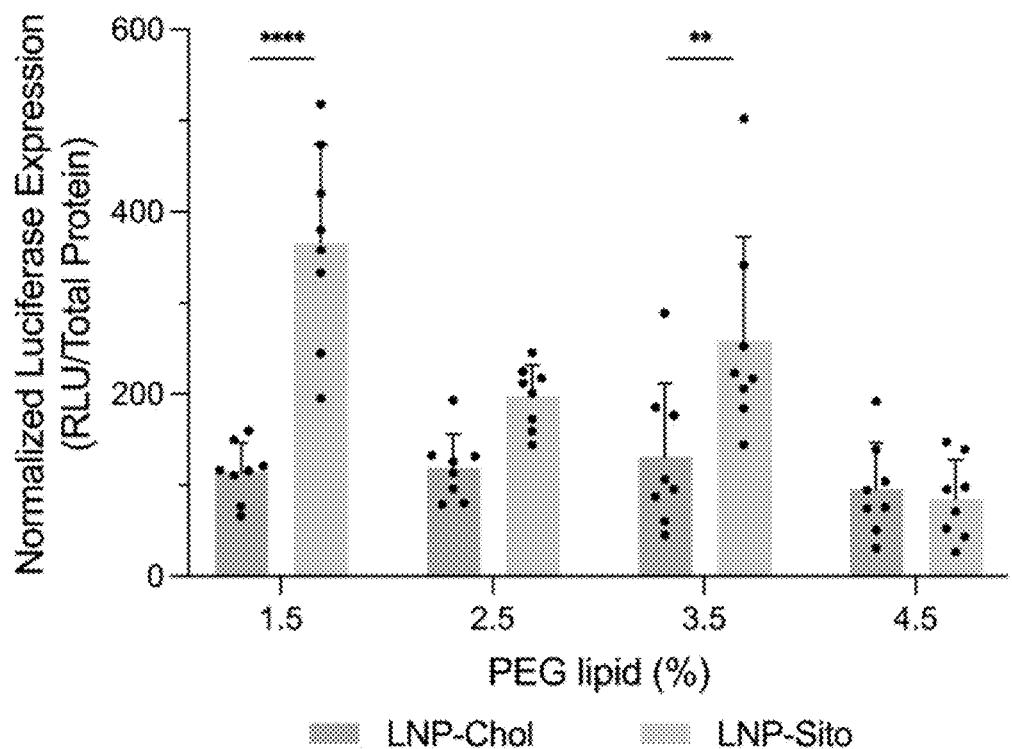

FIG. 28 is a graph of normalized luciferase expression versus percentage of PEG lipid, illustrating normalized Nluc expression in mouse lung homogenates harvested from BALB/c mice at 24 hours after inhalation of LNP-Chol (left columns) and LNP-Sito (right columns) containing Nluc mRNA and various amount of PEG lipid. Data is presented in mean±standard deviation. **$p<0.001$, $p<0.01$; significant analysis by two-way ANOVA with Sidak's multiple comparison test (n=8).

Figure 29:
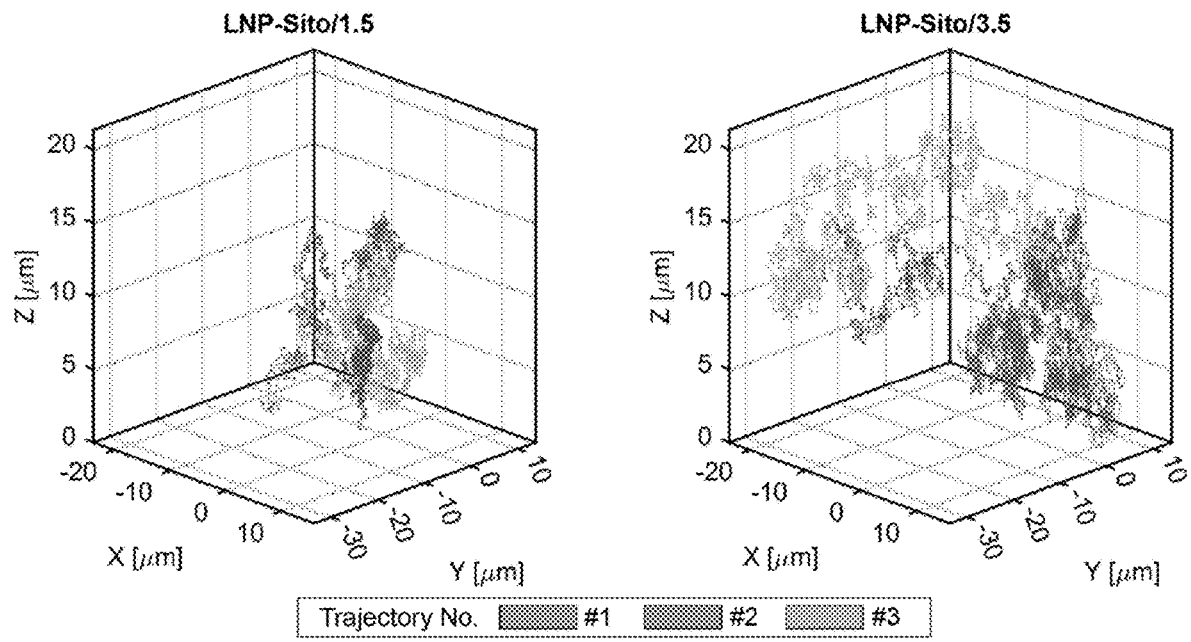

FIG. 29 provides 3D plots, illustrating three 40 second-long representative trajectories of LNP-Sito/1.5 and LNP-Sito/3.5 calculated using 3D-SMART. The measured 3D position is plotted at 1 ms temporal resolution.

Figure 30:
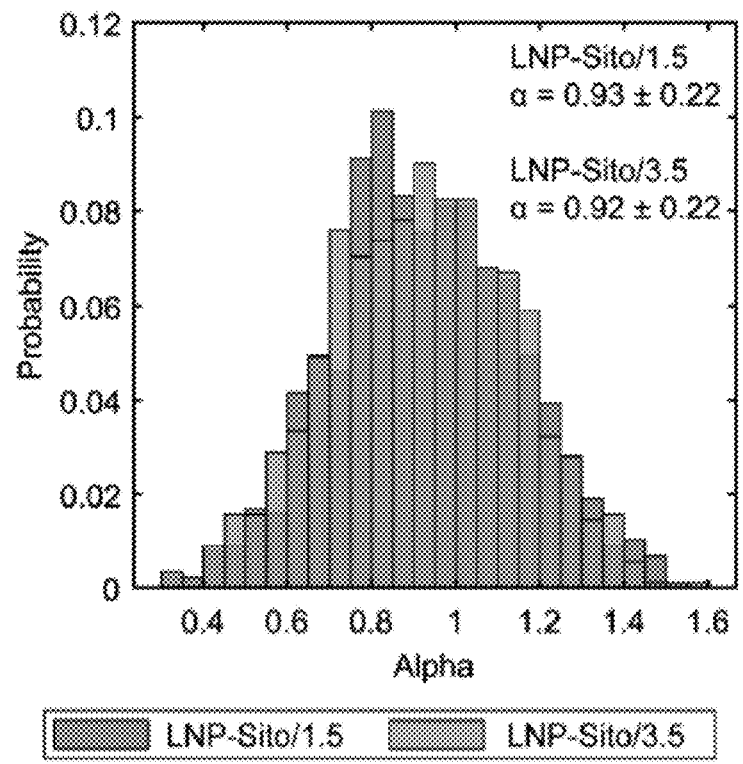

FIG. 30 is a plot of probability versus alpha, illustrating the alpha comparison of LNP-Sito/1.5 (dark) and LNP-Sito/3.5 (light) of the respective trajectories and showing that there is no significant difference in the alpha values.

Figure 31:
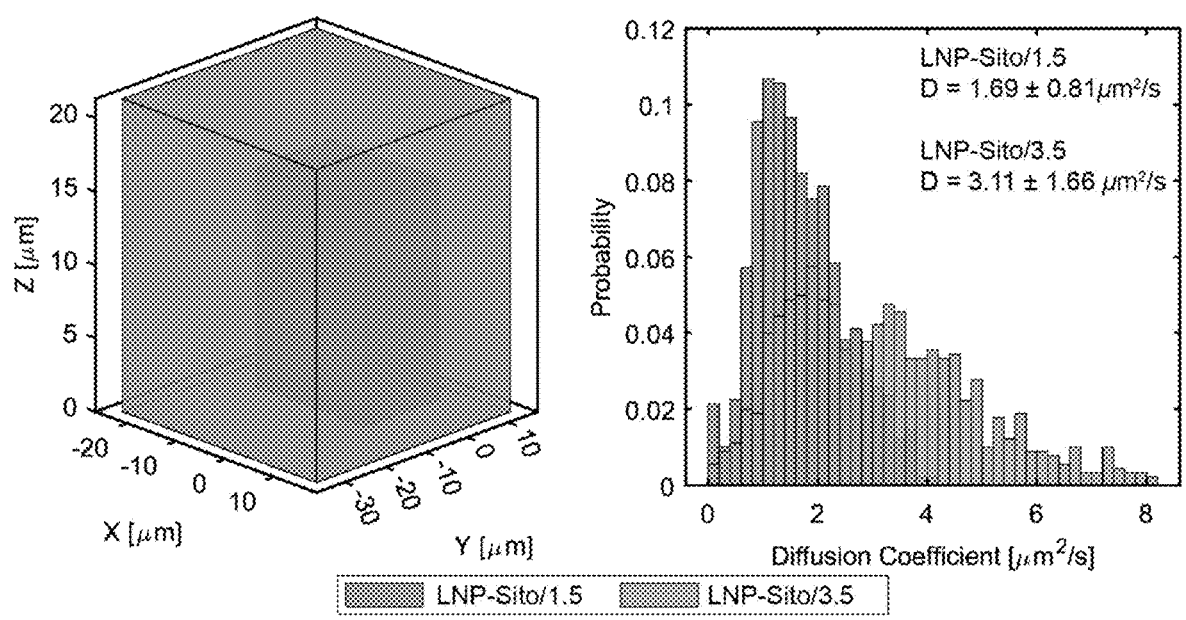

FIG. 31 is a plot illustrating the boundary of the representative trajectories drawn as boxes, demonstrating the dramatically increased travel range of the LNP-Sito/3.5 (lighter) compared to LNP-Sito/1.5 (darker) (left) and a plot providing an analysis of the trajectories for LNP-Sito/1.5 (darker, n=323) and LNP-Sito/3.5 (lighter, n=353) (right).

Figure 32:
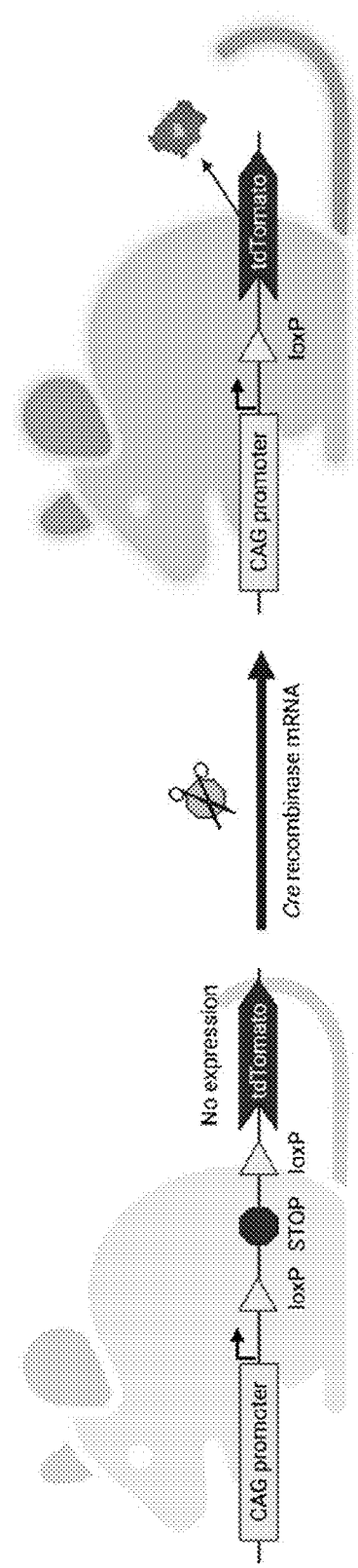

FIG. 32 is a schematic diagram illustrating the Cre-lox recombination in Ai9 transgenic Cre reporter mouse that expresses tdTomato when loxP recombination has occurred.

Figure 33:
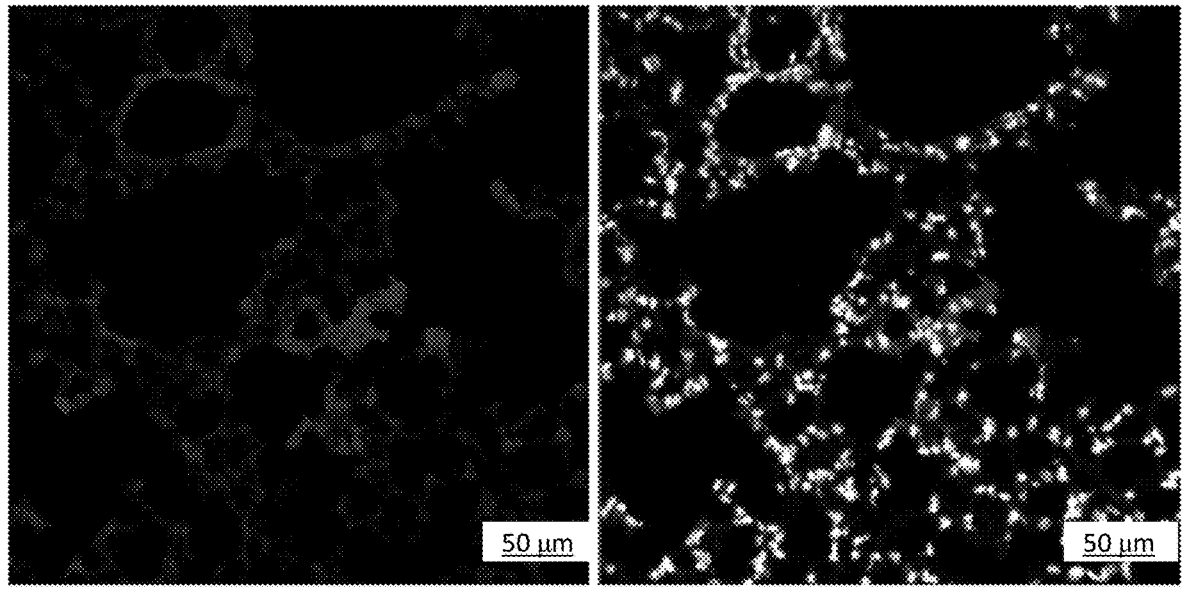

FIG. 33 provides digital images illustrating representative immunohistochemistry of Ai9 mouse lung sections displaying tdTomato expression after inhalation of nLNP encapsulating Cre mRNA. tdTomato (left) and nuclei (right) were detected in alveolar spaces.

Figure 34:
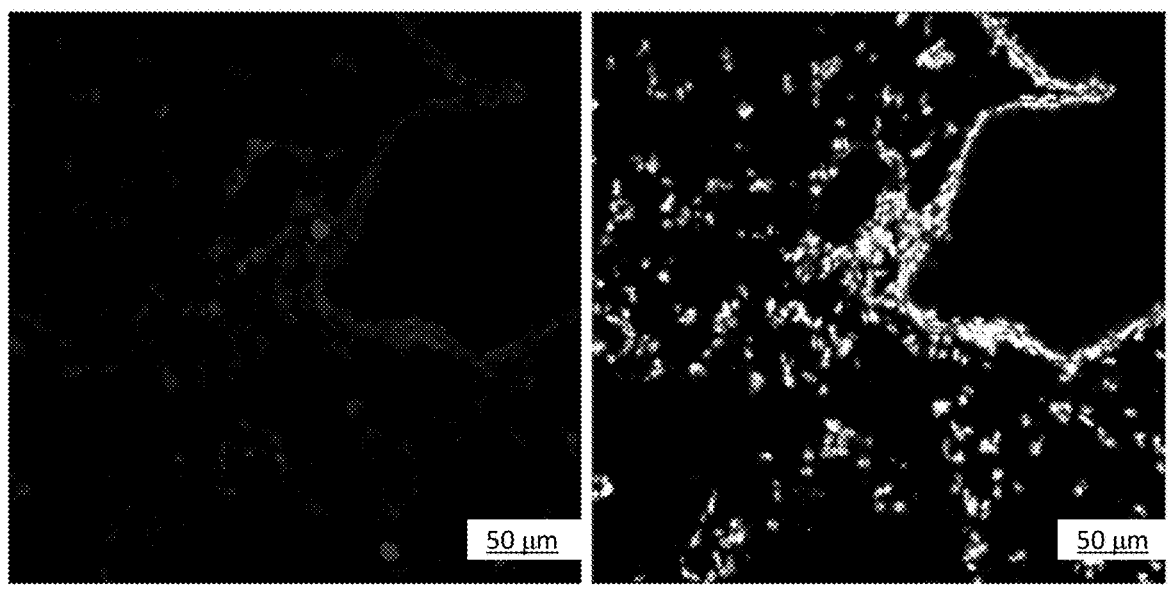

FIG. 34 provides digital images illustrating representative immunohistochemistry of Ai9 mouse lung sections displaying tdTomato expression after inhalation of nLNP encapsulating Cre mRNA. tdTomato (left) and nuclei (right) were detected in airway bronchioles.

Figure 35:
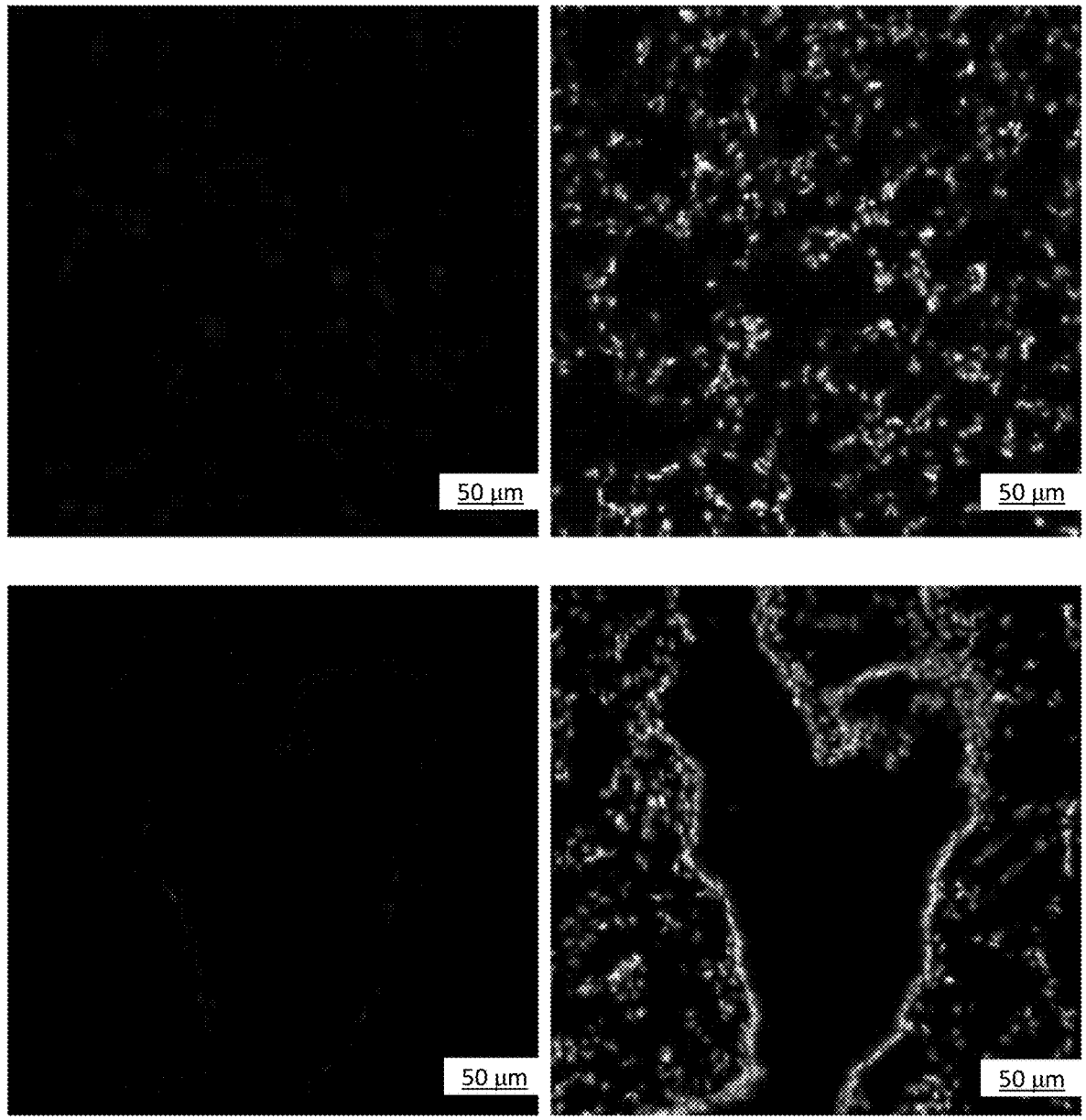

FIG. 35 provides digital images illustrating representative immunohistochemistry of Ai9 mouse lung sections without nanoparticle inhalation, with alveolar spaces and airway bronchioles presented with tdTomato (left) and the merged image (right).

Figure 36:
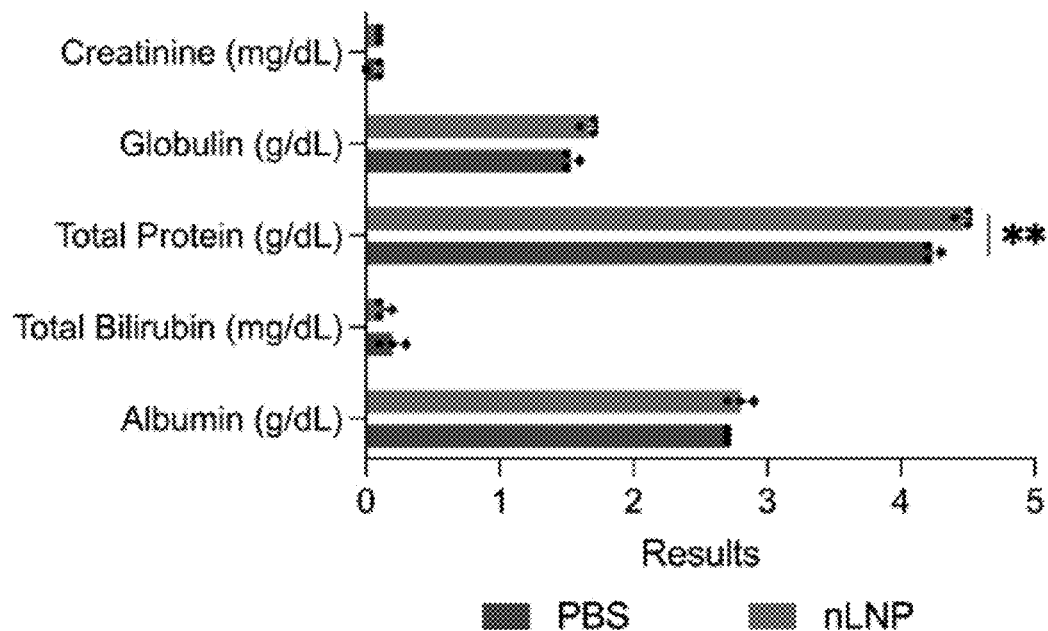

FIG. 36 is a plot illustrating the results from a clinical chemistry test of mouse sera harvested at 24 hours after PBS or nLNP inhalation.

Figure 37:
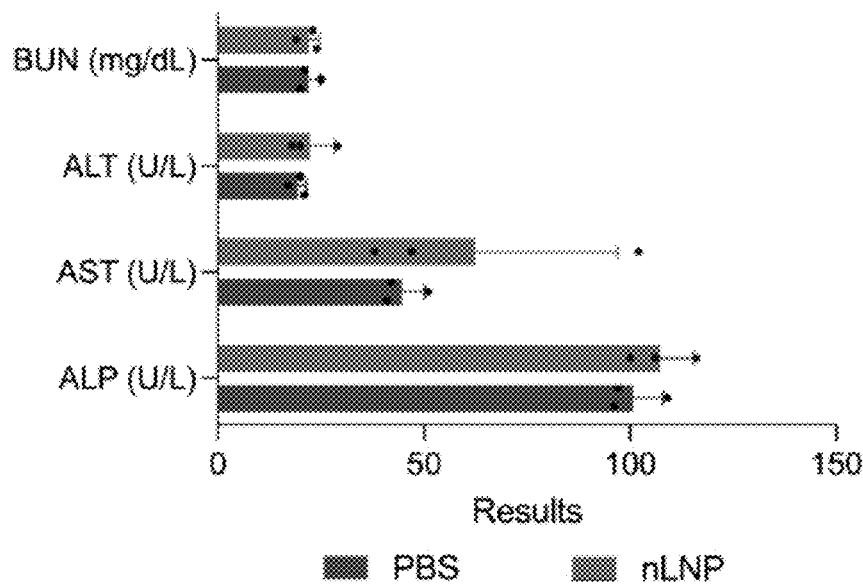

FIG. 37 is a plot illustrating additional results from the clinical chemistry test of mouse sera harvested at 24 hours after PBS or nLNP inhalation.

Figure 38:
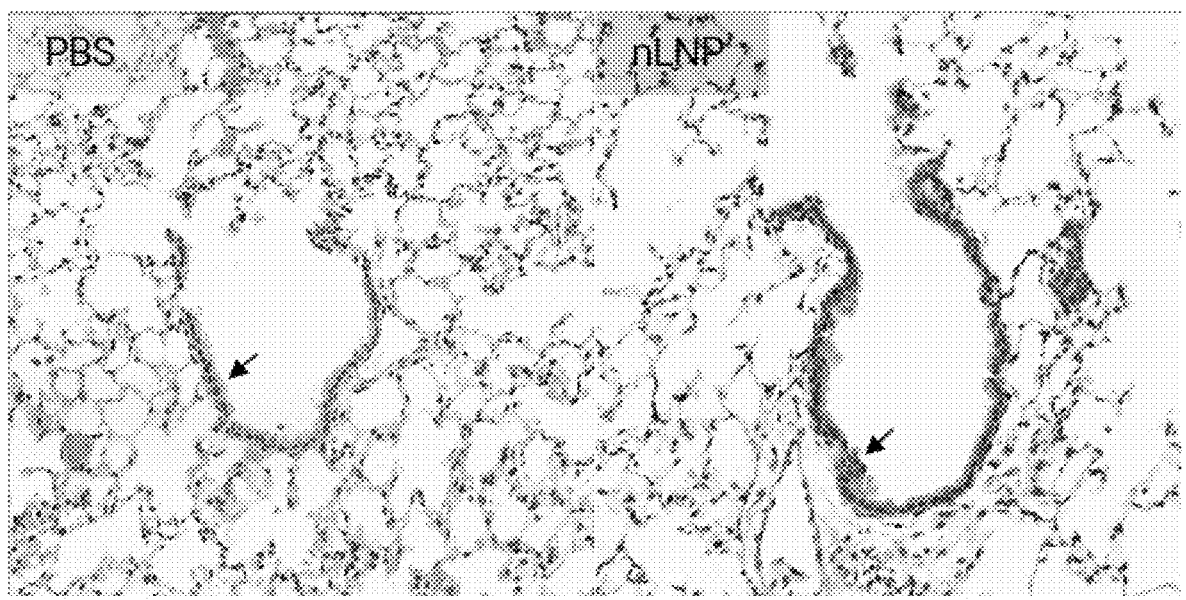

FIG. 38 provides additional digital images illustrating histopathological analysis of mouse lungs harvested at 24 hours after PBS (left) or nLNP (right) inhalation and stained with hematoxylin and eosin, with arrows indicating the bronchial epithelium.

Figure 39:
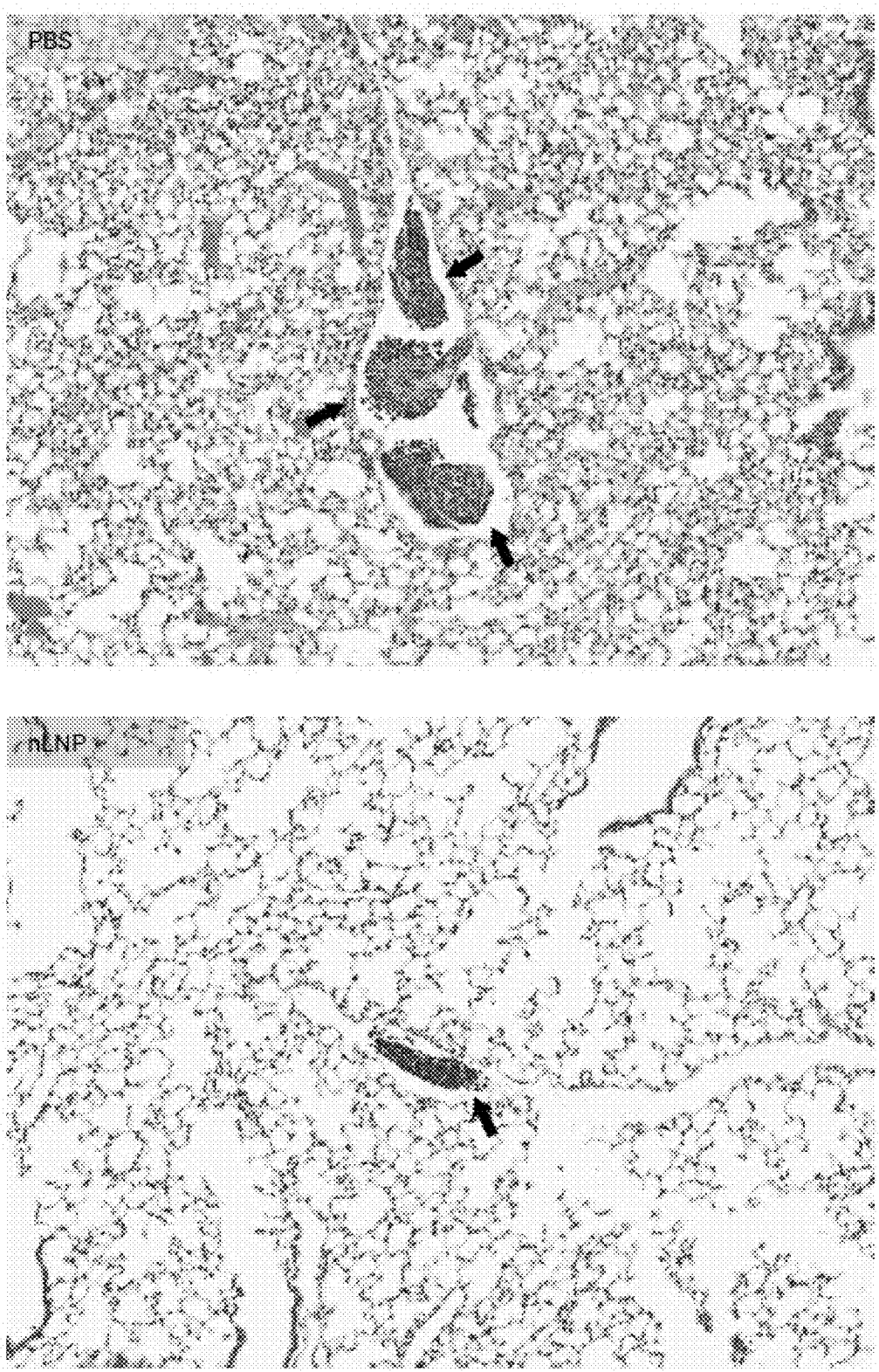

FIG. 39 provides digital images from histopathological analysis of the lung sections exposed to PBS or nLNP and stained with hematoxylin and eosin, illustrating that PBS- (top) and nLNP- (bottom) treated lungs had mononuclear clots (arrows).

Figure 40:
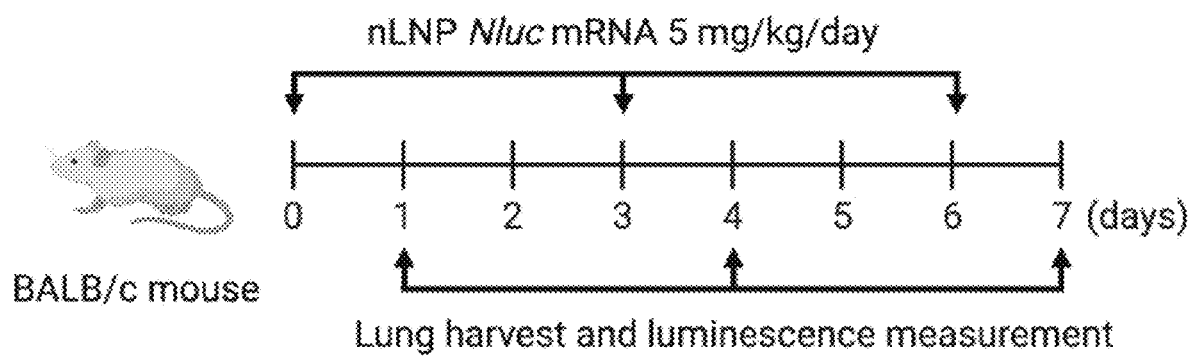

FIG. 40 is a schematic diagram, illustrating a dosing regimen for persistent inhalation of nLNP encapsulating Nluc mRNA.

Figure 41:
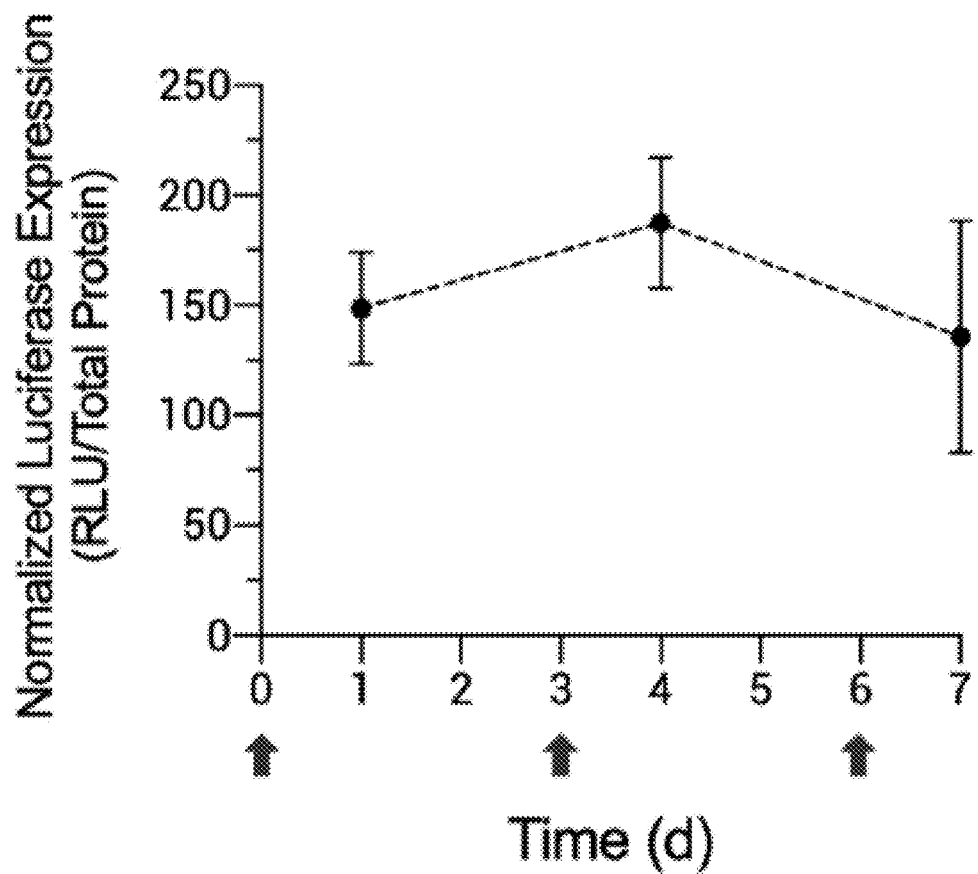

FIG. 41 is a graph of normalized luciferase expression versus time, illustrating the luciferase expression in mouse lungs of BALB/c after repeat dosing illustrated by the arrows.

Figure 42:
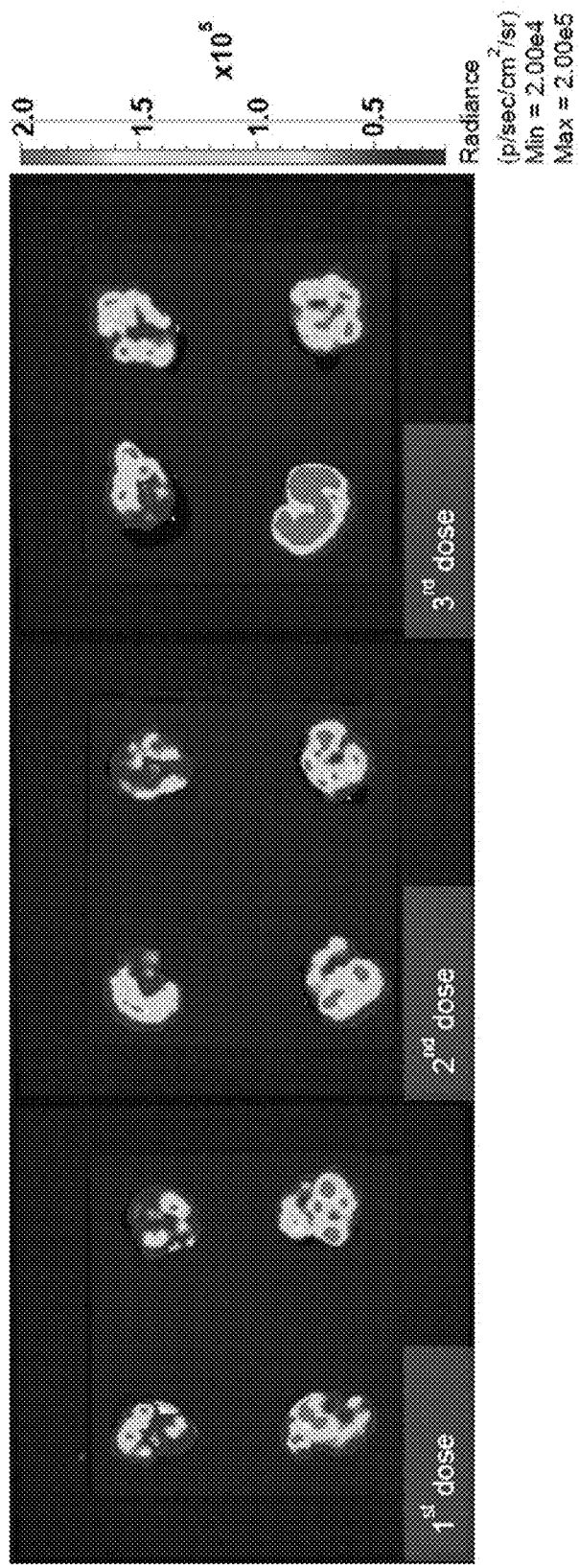

FIG. 42 provides digital images illustrating the ex vivo luminescence of mouse lungs that were harvested after three inhalations of nLNP encapsulating Nluc mRNA.

Figure 43:
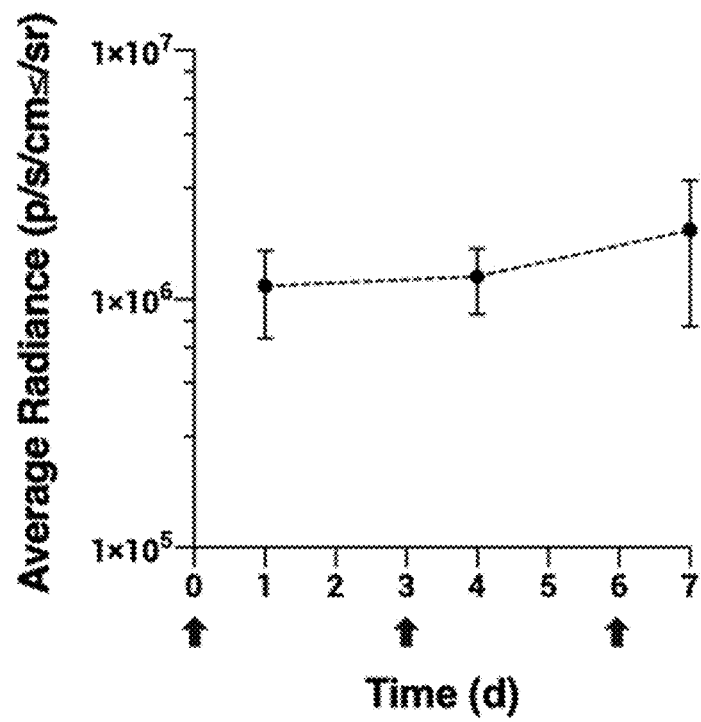

FIG. 43 is a graph of average radiance versus time, illustrating the average radiance of the luminescence in the images in FIG. 42.

Figure 44:
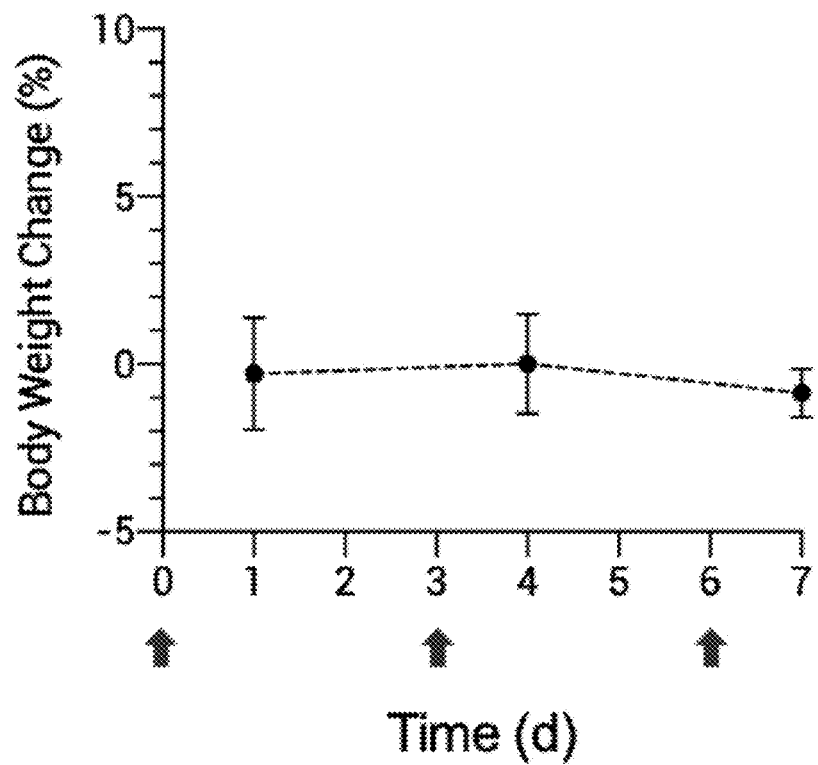

FIG. 44 is a graph of body weight versus time, illustrating the body weight change of BALB/c after repeat dosing shown by the arrows.

Figure 45:
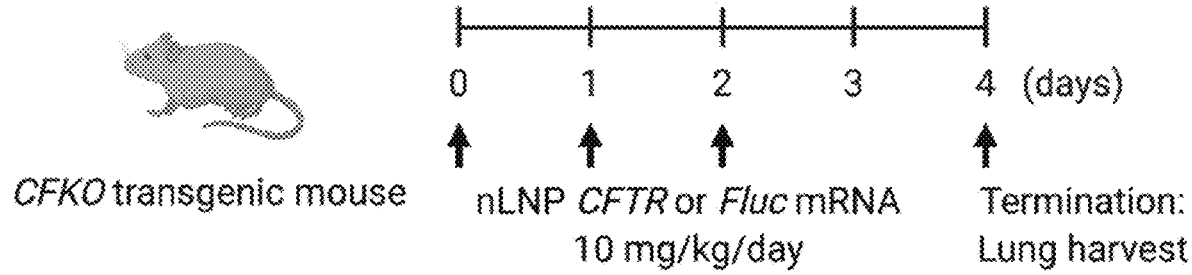

FIG. 45 is a schematic diagram illustrating a dosing regimen for CFTR mRNA delivery via inhalation.

Figure 46:
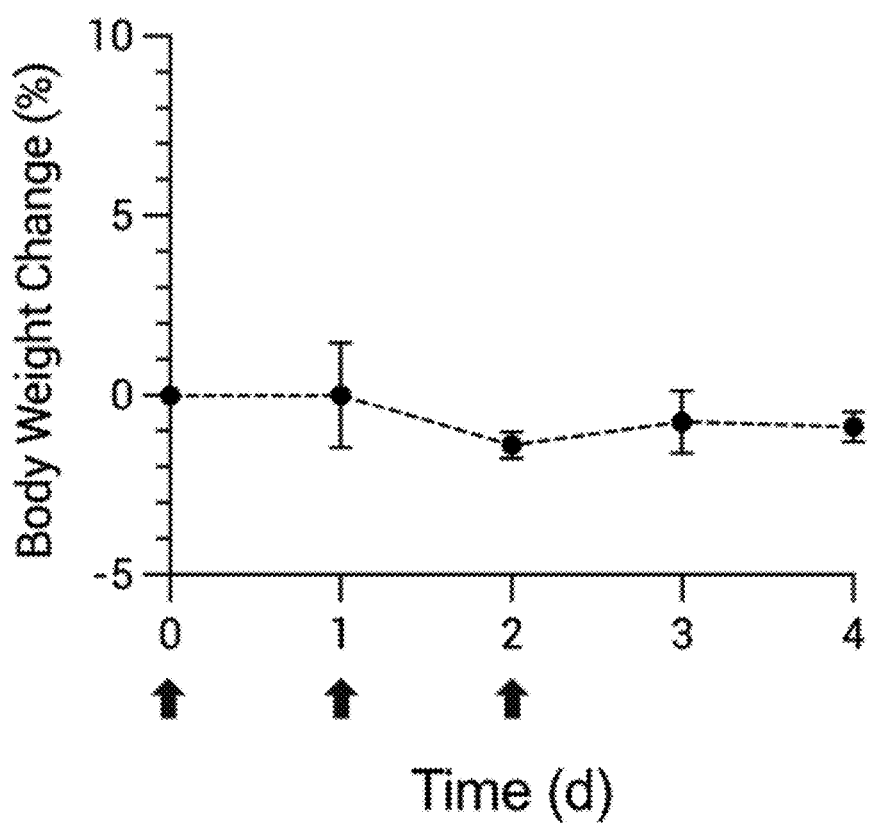

FIG. 46 is a graph of body weight versus time, illustrating the body weight changes of CFKO transgenic mice after repeat dosing shown by the arrows.

Figure 47:
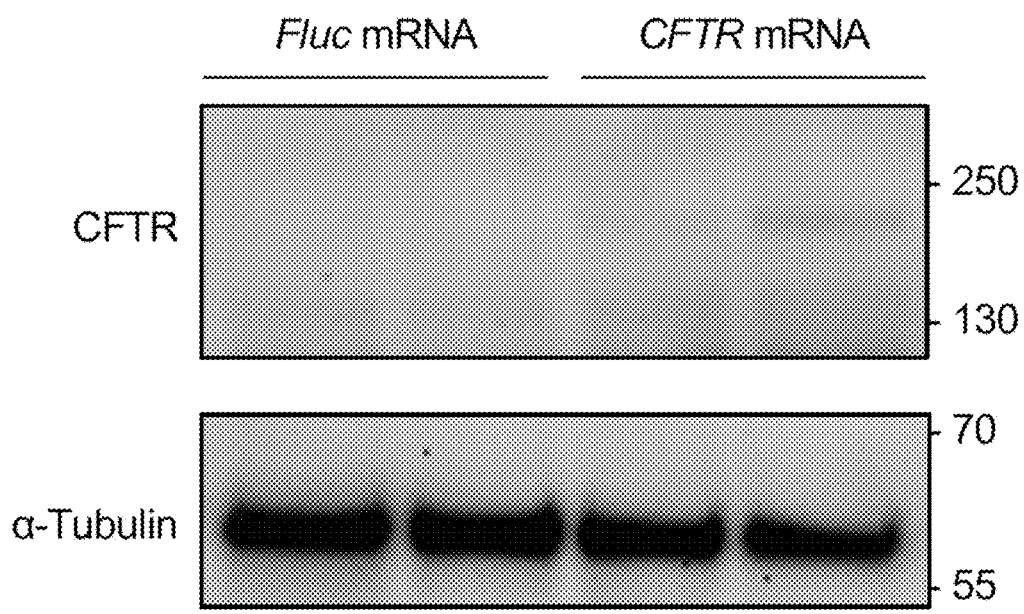

FIG. 47 provides digital images illustrating Western blot images after immunoprecipitation using an anti-CFTR antibody.

Figure 48:
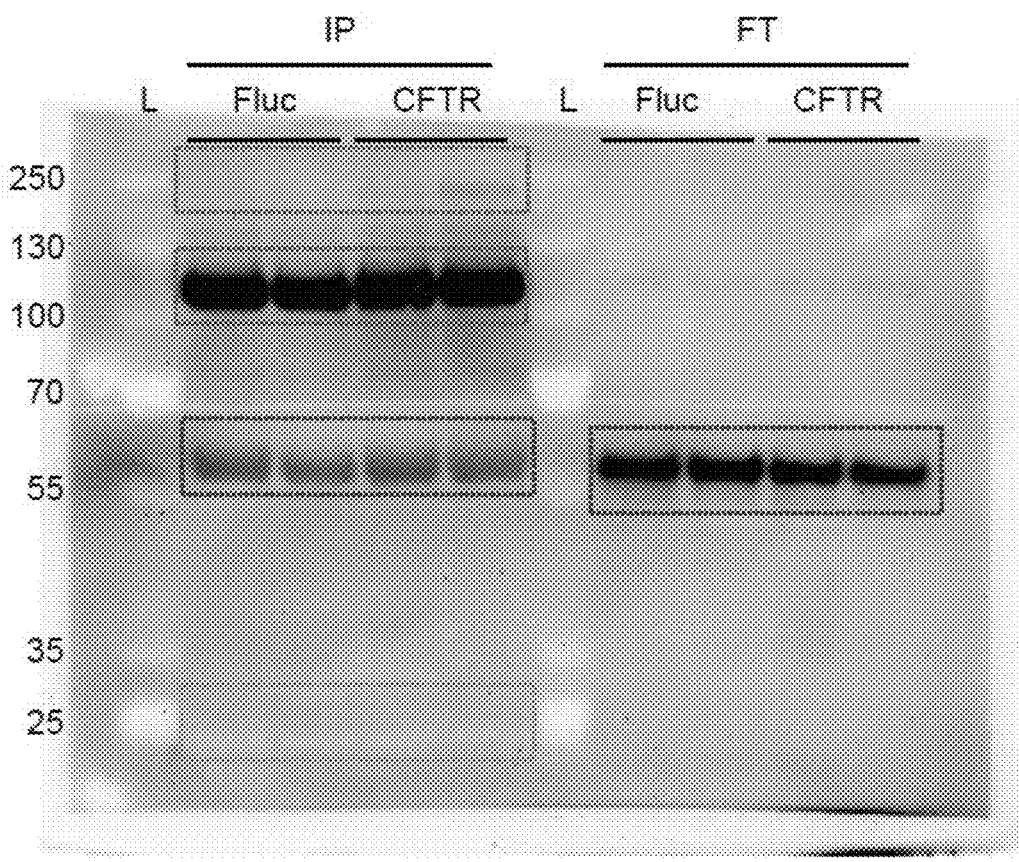

FIG. 48 is a digital image of a Western blot following immunoprecipitation (IP) against hCFTR after inhalation of nLNP encapsulating hCFTR or Fluc mRNA. IP; immuno-precipitated samples, FT; flow-through samples, L; ladders.

Figure 49:
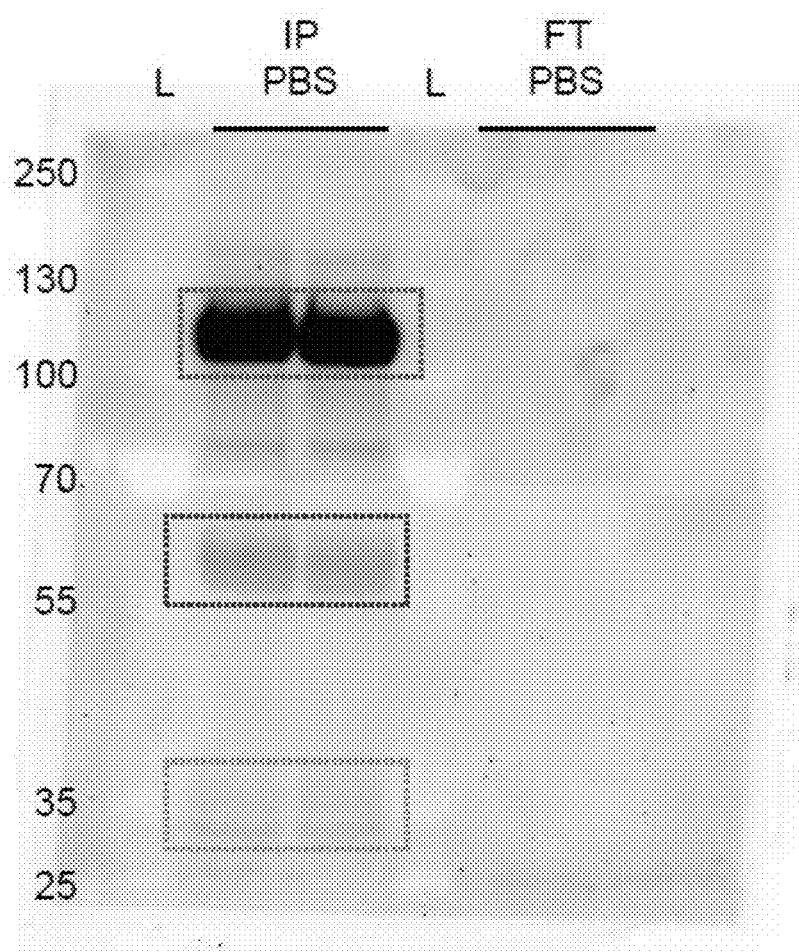

FIG. 49 is a digital image of a Western blot following immunoprecipitation (IP) of PBS as a control.

DETAILED DESCRIPTION

I. Definitions and Statements

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

"Cholesterol derivative" is a compound that has a substantially similar core structure to that of cholesterol, but has one or more atoms replaced by another atom or group. In some embodiments, a cholesterol derivative has an additional alkyl side chain, relative to cholesterol.

"Lipid" refers to an organic compound that is readily soluble in nonpolar solvents such as hydrocarbons, but typically is sparingly or non-soluble in water, and may be poorly soluble in other polar solvents. Ionizable lipids are lipids that can be ionized, for example, with pH-dependent ionization. The lipid may be anionic and/or cationic, for example, it may form an anion and/or a cation depending on pH. In some embodiments, an ionizable lipid may be positive at low pH, and may be substantially neutral at physiological or neutral pH.

"Nanoparticle" as used herein refers to a composition having a particle size (for example, a diameter) of from 1 to 1000 nanometers, such as from 1 to 750 nanometers, from 1 to 500 nanometers, from 1 to 250 nanometers, or from 1 to 100 nanometers. In some disclosed embodiments, Nanoparticle compositions include, but are not limited to, lipid nanoparticles (LNPs).

"Lipid nanoparticle" (LNP) refers to a nanoparticle comprising one or more lipid compounds. Typically, the lipid compound(s) will be a major component of the nanoparticle. LNPs may be substantially spherical in shape. Disclosed LNPs may be positively charged in low pH and substantially neutral at physiological pH. Alternatively, the LNP may be uncharged, even if the lipids themselves are charged. In some embodiments, the ionizable lipid is contained in the core and its charge may be shielded by other lipid components.

"Nucleic acid" refers to a polynucleotide molecule. The polynucleotide may be a naturally occurring polynucleotide or a synthetic polynucleotide. A nucleic acid may be a DNA, RNA or mixture of DNA and RNA nucleotides. Typically, the nucleic acid contains from 20 to 10,000 nucleotides or more, such as from 100, 200, 300, 400, 500, 600, 700, 800, 900, 1000, 2000, 3000, 4000, or 5000 nucleotides to 10,000 nucleotides.

Exemplary nucleic acids include, but are not limited to, single stranded DNA, single stranded RNA, double stranded DNA, RNA-RNA hybrid, DNA-RNA hybrid, shortmer, antagomir, antisense, ribozyme, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), or a combination thereof.

"Peptide" refers to a compound comprising amino acid residues connected by peptide bonds. Typically a peptide compound has from 2 to about 50 amino acid residues.

"Polypeptide" refers to a compound comprising amino acid residues connected by peptide bonds. When the amino acids are alpha-amino acids, either the L-optical isomer or the D-optical isomer can be used. In some embodiments, a polypeptide has from about 50 amino acid residues to 2000 or more amino acid residues.

"Protein" refers to a molecule or complex comprising one or more polypeptides having secondary, tertiary and/or quaternary structure. The secondary, tertiary and/or quaternary structure of a protein typically is stabilized using non-covalent bonds, such as ionic bonds, hydrogen bonds, hydrophobic interactions, and/or van der Walls interactions. Additionally, or alternatively, a protein may include disulfide bonds, such as between the thiol groups of cysteine residues.

"Small Molecule" refers to a organic molecule having a molecular weight of about 2000 Daltons or less. In some embodiments, the term "small molecule" refers to a compound that is not a polypeptide, protein, or nucleic acid molecule. A small molecule may be a small molecule therapeutic and/or prophylactic, such as an antibiotic, anti-inflammatory, anticancer, antiviral, immunosuppressant, analgesic, antifungal, antiparasitic, anticonvulsants, antidepressant, anti-anxiety, anti-psychotic, and the like.

"Subject" refers to mammals and other animals, particularly humans. Thus disclosed methods are applicable to both human therapy and veterinary applications.

II. Overview

Figure 1:
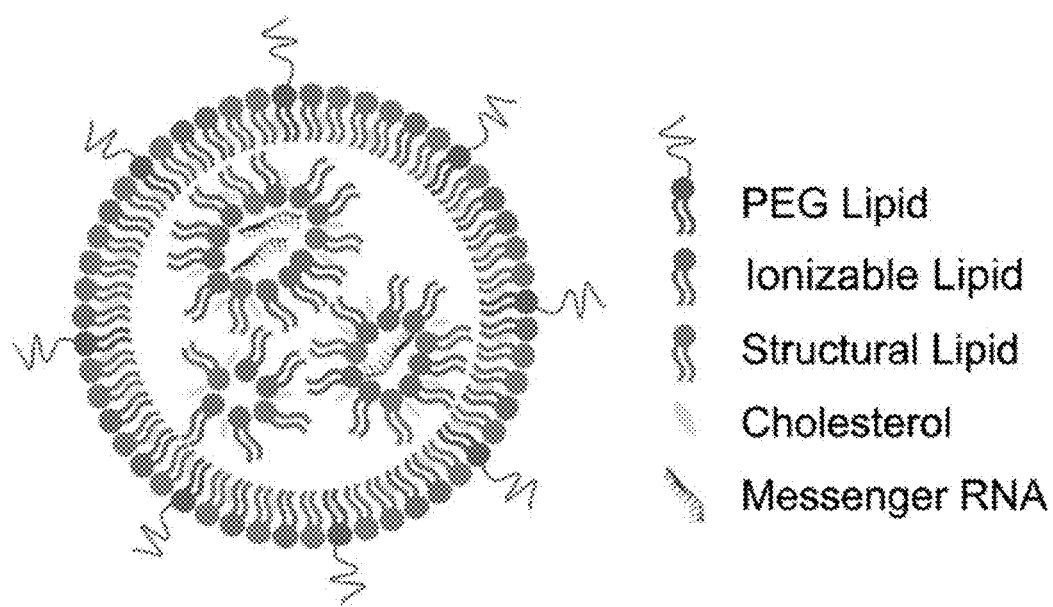
Figure 2:
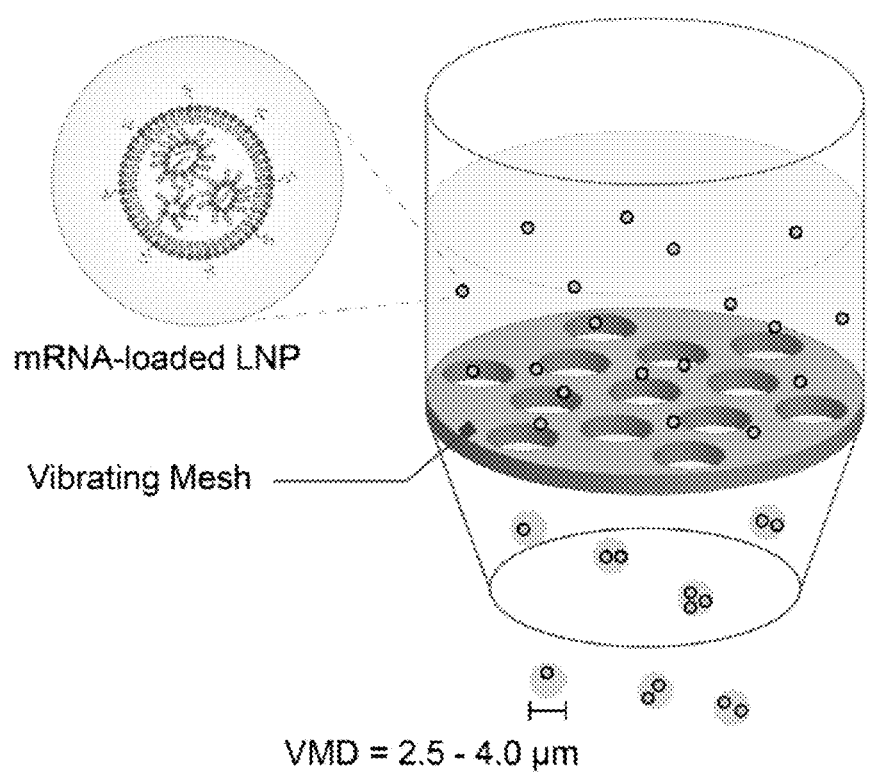
Figure 3:
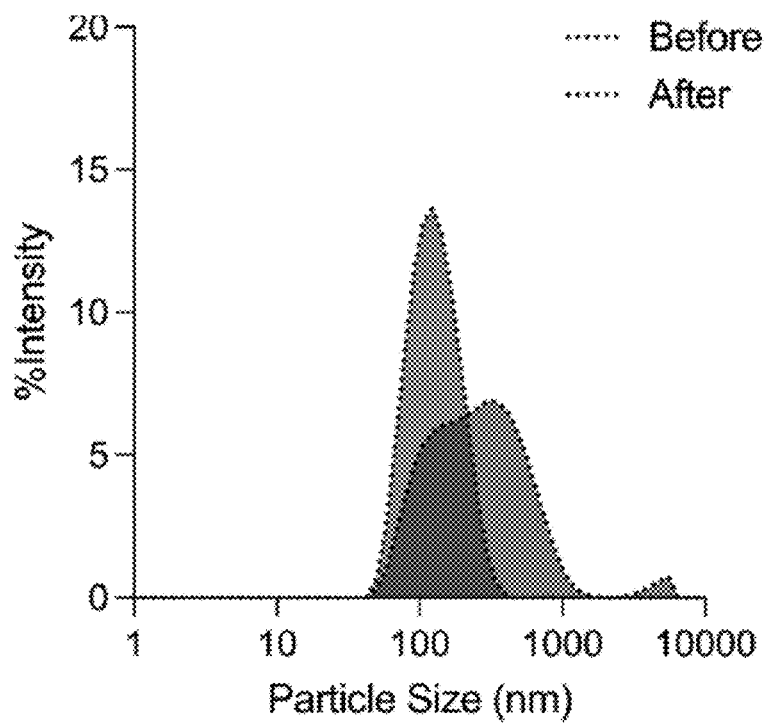

Recent clinical successes of mRNA-based vaccines proved that lipid nanoparticles (LNP; FIG. 1) can deliver mRNA to humans. LNP's ability to deliver mRNA to the inside of cells is not limited to vaccination and is more versatile in treating many genetic disorders. In fact, LNP has been extensively investigated to deliver mRNA therapies targeting various genetic diseases. Recently, LNP was employed in the clinical trial to deliver Cas9 mRNA and guide RNA for editing the gene causing transthyretin amyloidosis. However, therapeutic application of the LNP platform is restricted mostly for hepatic diseases because LNP innately accumulates in the liver when administered systemically, which significantly limits access to other organs. Despite recent studies showing that modulating nanoparticle surface charge permits the systemically administered LNP to reach the lungs, focused delivery of mRNA therapy to the pulmonary system via inhalation still represents a promising route to achieve lung transfection. Inhaled LNP encapsulating mRNA can access the pulmonary system, particularly lung epithelium, avoiding potential off-target effects in other organs. For LNP inhalation, a vibrating mesh nebulizer, which turns a liquid into a mist, could be useful due to its ability to generate a uniform aerosol and its compatibility with aqueous biopharmaceutical (FIG. 2). However, LNP undergo (1) considerable shear force in the nebulizer, leading to the destruction of the nanoparticle structure and genetic payloads (FIG. 3). Nebulized LNP then encounter biological barriers that limit entry of all gene therapy vectors into the lungs: (2) the airway mucus that impedes the nanoparticles from reaching epithelial cells, and (3) inadequate cytosolic availability of mRNA after uptake by cells due to endosomal entrapment. Hence, there is a need for new LNP formulations capable of overcoming aforementioned barriers and delivering mRNA to the lungs.

Typical LNP contains four functional lipids that play distinctive roles: (1) ionizable lipid, (2) PEG lipid, (3) cholesterol, and (4) structural lipid (FIG. 1). The chemistry of ionizable lipids has been of primary interest due to its significance in transfection efficiency; however, the robustness of the LNP membrane is primarily associated with the other lipids. Specifically, cholesterol impacts the biophysical properties of unsaturated lipid membranes by increasing the rigidity of the bilayer. Besides, substituting cholesterol with its C-24 alkyl phytosterols or its oxidized derivatives in LNP enhances intracellular delivery of mRNA, suggesting the important roles of sterols in endosomal escape. PEG lipid prevents LNP from aggregation and improves particle stability by providing steric hindrance. Amount of PEG lipid in LNP is also related to the resulting particle size. As shown in recent studies, the presence of a dense PEG layer helps LNP to achieve pulmonary delivery of mRNA following nebulization. Furthermore, PEG density affects the Brownian motion of nanoparticles, thereby changing the particle mobility in mucus. Yet, the PEG layer inhibits the receptor-mediated endocytosis by reducing adsorption of serum protein and interferes with the endosomal escape of LNP, significantly restricting the intracellular delivery of mRNA. Therefore, successful pulmonary delivery of mRNA via LNP nebulization may require opposing particle characteristics: particle stabilization and mucus penetration are achievable by a dense PEG layer, whereas subcellular delivery of mRNA relies on a light PEG layer. To meet such criteria, a cholesterol derivative, such as β-sitosterol, may be useful.

Disclosed herein are embodiments of a nanoparticle composition comprising a cholesterol derivative and high PEG content that enable nebulization, mucus penetration, and endosomal escape of LNP. A new LNP formulation was identified by screening a small library that was compliant with nebulization and was named nebulizable LNP (nLNP). This nLNP retained its physicochemical properties and efficiently delivered an exemplary therapeutic mRNA after nebulization. The nLNP delivered mRNA to the lung epithelia with high efficiency in a non-invasive and direct manner.

III. Composition

A. Nanoparticle

Disclosed herein is a lipid nanoparticle suitable for nebulization. In some embodiments, the nanoparticle comprises an ionizable lipid, a cholesterol derivative, a structural lipid, and a PEG lipid.

In some embodiments, the ionizable lipid is DLin-MC3-DMA, 1-Linoleoyl-2-linoleyloxy-3-dimethylaminopropane (DLin-2-DMAP), 1,2-Dilinoleylcarbamoyloxy-3-dimethylaminopropane (DLin-C-DAP), 1,2-Dilinoleoyl-3-dimethylaminopropane (DLin-DAP), 1,2-Dilinoleyloxy-N,N-dimethylaminopropane (DLinDMA), 2,2-Dilinoleyl-4-dimethylaminomethyl-[1,3]-dioxolane (DLin-K-DMA), 2,2-dilinoleyl-4-(2-dimethylaminoethyl)-[1,3]-dioxolane (DLin-KC2-DMA), (6Z,9Z,28Z,31Z)-heptatriaconta-6,9,28,31-tetraen-19-yl 4-(dimethylamino)butanoate (DLin-MC3-DMA), 1,2-dioleoyl-3-dimethylammonium propane (DODAP), N,N-dimethyl-(2,3-dioleyloxy)propylamine (DODMA), dioctadecylamidoglycyl carboxyspermine (DOGS), Spermine cholesterylcarbamate (GL-67), bis-guanidinium-spermidine-cholesterol (BGTC), 3β-(N(N',N'-dimethylaminoethane)-carbamoyl)cholesterol(DC-Chol), 1,1'-(2-(4-(2-((2-(bis(2-hydroxydodecyl)amino)ethyl)(2-hydroxydodecyl)amino)ethyl)piperazin-1-yl)ethylazanediyl) didodecan-2-ol (C12-200), N-t-butyl-N'-tetradecylaminopropionamidine (diC14-amidine), Dimethyldioctadecylammoniumbromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride (DODAC), Dioleyloxypropyl-3-dimethyl hydroxyethyl ammonium bromide (DORIE), N-(1-(2,3-dioleyloxyl)propyl)-N-2-(sperminecarboxamido)ethyl)-N,N-dimethylammonium trifluoracetate (DOSPA), 1,2-dioleoyltrimethyl ammonium propane chloride (DOTAP), N-(1-(2,3-dioleyloxy)propyl)-N,N,N-trimethylammonium chloride (DOTMA), ALC-0159 (α-[2-(ditetradecylamino)-2-oxoethyl]-ω-methoxy-poly(oxy-1,2-ethanediyl), Cas #1849616-42-7), cKK-E12 (3,6-bis[4-[bis(2-hydroxydodecyl)amino]butyl]-2,5-piperazinedione, CAS #1432494-65-9), ALC-0315 (2-hexyl-decanoic acid, 1,1'-[[(4-hydroxybutyl)imino]di-6,1-hexanediyl] ester, CAS #2036272-55-4), 9A1P9 (2-(dioctylamino)ethyl nonyl hydrogen phosphate), SM-102 (8-[(2-hydroxyethyl)[6-oxo-6-(undecyloxy)hexyl]amino]-octanoic acid, 1-octylnonyl ester, CAS #2089251-47-6, FTT5 (CAS #2328129-27-5), L-319 (9-[4-(dimethylamino)-1-oxobutoxy]-heptadecanedioic acid, 1,17-di-(2Z)-2-nonen-1-yl ester, CAS #1351586-50-9), 306Oi10 (tetrakis (8-methylnonyl) 3,3',3''',3'''-(((methylazanediyl)bis (propane-3,1-diyl))bis(azanetriyl))tetrapropionate, CAS #2322290-93-5), or a combination thereof. In some embodiments, the ionizable lipid is DLin-MC3-DMA.

In some embodiments, the cholesterol derivative is any cholesterol derivative that facilitates formation of the nanoparticle and mRNA encapsulation and delivery by nebulization. In some embodiments, the cholesterol derivative is β-sitosterol, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β-[N—(N'N'-dimethylaminoethyl)carbamoyl cholesterol (DC-Chol), 24(S)-hydroxycholesterol, 25-hydroxycholesterol, 25(R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-cholesteryl-3e-ol, dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol, or fecosterol, or a salt or ester thereof, or a combination thereof. In some embodiments, the cholesterol derivative is β-sitosterol.

In some embodiments, the structural lipid is 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), or a combination thereof. In some embodiments, the structural lipid is 1,2-distearoyl-sn-glycero-3-phosphocholine (DSPC).

In some embodiments, the PEG lipid is PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, a PEG lipid may be PEG-c-DOMG, PEG-DMG, PEG-DLPE, PEG-DMPE, PEG-DPPC, PEG-DSPE, or a combination thereof. In any embodiments, the PEG chain may have a molecular weight of from about 1000 daltons to about 20,000 daltons or more. In some embodiments, the PEG lipid is 1,2-dimyristoyl-rac-glycerol-methoxy(poly(ethylene glycol)-2000 (DMG-PEG$_{2K}$).

In some embodiments, the nanoparticle comprises from 30% to 65% of the ionizable lipid, from 30% to 60% of the cholesterol or cholesterol derivative, from 5% to 20% of the structural lipid, and from 1.5% to 12.5% of the PEG lipid, in amounts relative to each other, and such that the amounts of ionizable lipid, cholesterol or cholesterol derivative, structural lipid, and PEG lipid totals 100%.

In some embodiments, the ionizable lipid is present in the nanoparticle in an amount of from 30% to 65%, such as from 45% to 60%, from 45% to 55%, or 30% to 45%, relative to the other components.

In some embodiments, the cholesterol or cholesterol derivative is present in the nanoparticle in an amount of from 30% to 60%, such as from 30% to 45%, from 37% to 42%, from 37% to 40%, or 40% to 60% relative to the other components.

In some embodiments, the structural lipid is present in the nanoparticle in an amount of from 5% to 20%, such as from 7% to 12%, or from 12% to 20%, relative to the other components.

In some embodiments, the PEG lipid is present in the nanoparticle in an amount of from 1.5% to 12.5%, such as from 1.5% to 10%, from 1.5% to 8%, from 1.5% to 7.5%, from 2% to 12.5%, from 3% to 12.5%, from 4% to 12.5%, or from 4% to 8%, relative to the other components.

In some embodiments, the nanoparticle consists essentially of, or consists of, from 30% to 65% of an ionizable lipid, from 30% to 60% of a cholesterol derivative, from 5% to 20% of a structural lipid, and from 1.5% to 12.5% of a PEG lipid, in amounts relative to each other. In some embodiments, the term 'consisting essential of', with respect to the nanoparticle, excludes additional structural components of the nanoparticle, such as, for example, additional lipids. The term does not exclude the presence of one or more therapeutic agents.

B. Pharmaceutical Formulation

Also disclosed herein are embodiments of a pharmaceutical formulation comprising a therapeutic agent and a nanoparticle disclosed herein. The formulation may be useful for delivering the therapeutic agent to a subject. In some embodiments, the therapeutic agent is at least partially encapsulated within the nanoparticle, and maybe fully encapsulated in the nanoparticle.

Typically, the nanoparticles are prepared in a liquid formulation for nebulization. Suitable liquid carriers include any carrier suitable for nanoparticle preparation and subsequent nebulization. Exemplary carriers include, but are not limited to, balanced salt solution (BSS), such as plasma-activated saline (Pas), Hanks' Balanced Salt Solution (HBSS), Earle's Balanced Salt Solution (EBSS), Gey's Balanced Salt Solution, Tris-Buffered Saline (TBS), and Ringer's balanced salt solution (RBSS), and isotonic saline, such as HEPES-buffered saline and Ringer's solution.

The therapeutic agent may be any therapeutic agent suitable for encapsulation in the nanoparticle and delivered to a subject. The therapeutic agent may be a nucleic acid agent such as mRNA or DNA, protein, polypeptide, small molecule therapeutic, and the like. In some embodiments, the therapeutic agent is, or comprises, a nucleic acid. The nucleic acid being present in the disclosed formulation includes known any type of nucleic acid. The nucleic acid may be described as a therapeutic and/or prophylactic nucleic acid. Nucleic acid can be any single stranded DNA or RNA, either double-stranded DNA or the RNA-RNA or DNA-RNA hybrids; shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), single guide RNA (sgRNA) and mixtures thereof.

In some embodiments, the nucleic acid is mRNA. Example mRNA suitable for use in the disclosed formulation include, but are not limited to, Firefly luciferase (Fluc), Nanoluciferase (Nluc), Human cystic fibrosis transmembrane conductance regulator (CFTR), Cre mRNA, EGFP mRNA, CRISPR-Cas9 nickase mRNA, base editor mRNA, prime editor mRNA, or a combination thereof.

In some embodiments, the formulation has greater than 90% nucleic acid encapsulation. As used herein, 90% encapsulation means that 90% of nucleic acids present in the solution exist within the particles and 10% exist outside the particles. In other embodiments, the formulation has a weight ratio between the mass of ionizable lipid and the mass of nucleic acid in the formulation of from 5 to 15, where the weight ratio is calculated as the mass of ionizable lipid (IL) divided by mass of nucleic acid (NA) (i.e., IL/NA).

IV. Examples

Materials:

Fluc mRNA, Cre mRNA, EGFP mRNA, Cy5-labelled EGFP, and hCFTR mRNA were purchased from TriLink Biotechnologies (CA, USA). Uridine of Fluc, Cre, EGFP, and Cy5-labelled EGFP mRNA was fully substituted with 5-methoxyuridine. Uridine and cytidine of hCFTR mRNA was fully substituted with pseudouridine and 5-methylcytidine, respectively. Cholesterol and β-sitosterol were purchased from Sigma-Aldrich (MO, USA). DMG-PEG$_{2K}$ was bought from NOF America. DLin-MC3-DMA and DSPC were obtained from BioFine International Inc. and Avanti Polar Lipids, Inc., respectively.

LNP Formulation and Characterization:

LNP composed of DLin-MC3-DMA, Cholesterol or β-sitosterol, DMG-PEG$_{2K}$, DSPC, and mRNA were prepared using microfluidic mixing. Briefly, mRNA was diluted in sterile 50 mM citrate buffer, and lipid components were prepared at 5.5 mM in 100% ethanol at a 50:38.5:1.5:10 molar ratio. The lipid and mRNA solutions were mixed using the NanoAssemblr Benchtop at a 1:3 ratio, followed by overnight dialysis against sterile PBS using a Slide-A-Lyzer G2 cassette with 10,000 Da molecular-weight-cut-off (Thermo Fisher, MA). Dialyzed LNP solutions were concentrated using Amicon® Ultra centrifugal filter units with 10,000 Da molecular-weight cut-off (Millipore). Hydrodynamic size and PDI of the LNP were measured in dynamic light scattering using the Zetasizer Nano ZSP (Malvern Instruments). mRNA encapsulation was assayed using a Quant-iT™ RiboGreen® RNA Assay kit (Thermo Fisher, MA) and a multimode microplate reader (Tecan Trading AG, Switzerland).

Cell Culture

HeLa and A549 were obtained from Prof. Robert Langer at MIT and Prof. Adam Alani at OSU. 16HBE14o- and CFBE41o-cells were obtained of Prof. Kelvin MacDonald at OHSU. HEK293T/17 was purchased from ATCC. SW480 and HT-29 were obtained of Prof. Melissa Wong at OHSU. HeLa and A549 cells were cultured in DMEM supplemented with 10% heat-inactivated FBS and 1% penicillin/streptomycin (Thermo Fisher, MA). SW480 and HT-29 cells were cultured according to the ATCC culture protocols. 16HBE14o- and CFBE41o-cells were cultured in MEM supplemented with 10% heat-inactivated FBS, and 1% penicillin/streptomycin/glutamine (Thermo Fisher, MA).

In Vitro Fluc mRNA Transfection Assay

For in vitro Fluc mRNA transfection assays, cells were seeded on a white 96 well plate at $4 \times 10^3$ cells/well, followed by overnight incubation for cell attachment. Cells were incubated with LNP encapsulating Fluc mRNA for 24 hours and analyzed for cell viability and luciferase activity with the ONE-Glo™+Tox luciferase reporter and cell viability assay kit (Promega) using a multimode microplate reader (Tecan Trading AG, Switzerland).

LNP Nebulization

Nebulization of LNP was performed as described. In brief, an Aeroneb® Lab Control Module equipped with a lab nebulizer unit (Aerogen, Ireland) was used to nebulize LNP. LNP solutions were added to the nebulizer unit, and the nebulized LNP were collected for analysis. For in vitro mRNA transfection, cells were seeded onto a 12 well plate at $5 \times 10^4$ cells/well and allowed to attach for overnight incubation. LNP were diluted with serum-free media and nebulized with a small nebulizer unit directly onto the seeded cells (1 µg/well), followed by 24-hour incubation. Cell viability and in vitro luciferase expression was assayed using ONE-Glo™+Tox luciferase reporter and cell viability assay kit (Promega) and a multimode microplate reader (Tecan Trading AG, Switzerland).

In Vitro Transcription of mRNA

A linearized plasmid containing nanoluciferase (Nluc) under the T7 promoter was used as a template for in vitro transcription. Nluc mRNA was synthesized using the HiScribe T7 High Yield RNA Synthesis Kit (New England Biolabs Inc., MA) and CleanCap® Reagent AG (TriLink Biotechnologies, CA) according to the manufacturer's instructions. Synthesized mRNA was purified using the Monarch® RNA Cleanup Kit (New England Biolabs) and stored at −80° C. Concentration of Nluc mRNA was measured using a multimode microplate reader (Tecan Trading AG, Switzerland). For agarose gel electrophoresis, 1 µg of IVT mRNA or RiboRuler high range RNA ladder (Thermo) were denatured and loaded on 1.5% agarose-formaldehyde gel prestained with GelRed (Biotium, CA). The gel was run at 85V for 2 hours, followed by UV visualization.

Animals

Female BALB/c mice were purchased from Charles River Laboratories (MA, USA). B6.Cg-Gt(ROSA)$^{26Sortm9(CAG-tdTomato)Hze}$/J (Ai9) mice were purchased from the Jackson Laboratory (JAX, 007909). Cftr$^{-/-tm1Unc}$ Tg(FABPCFTR)1Jaw/J bitransgenic CFKO mice were purchased from The Jackson Laboratory (JAX 002364). Mice exhibited full knockout of the endogenous mouse Cftr. To avoid intestinal complications, hCFTR was locally expressed under the rat fatty acid binding protein 2, intestinal gene promoter.

Pulmonary Nluc mRNA Transfection by LNP Inhalation

To assay pulmonary Nluc mRNA transfection in mice, a mouse nebulizer delivery system (Kent Scientific) was used. In brief, BALB/c mice (5-10 week old) were restrained in a tube rodent holder. The tube holder was attached to a plastic spacer connecting a nebulizer unit and airflow at 1 LPM (liter per minute). LNP solution was prepared at 0.5 mg mRNA per ml and added into the nebulizer unit at a rate of 25 µl per minute using a syringe pump. After 24 hours post-inhalation, mouse lungs were harvested, briefly washed with sterile PBS, and incubated in Nano-Glo® substrate (Promega) diluted 40-fold in PBS for 5 minutes at room temperature, followed by ex vivo bioluminescence imaging in IVIS® Lumina XRMS (PerkinElmer). After imaging, lungs were homogenized with sterile PBS and centrifuged at 17,000 g for 30 minutes at 4° C. to collect supernatants. 30 µl of the supernatants was incubated with 60 µl of Nano-Glo® substrate diluted 80-fold in PBS for 5 minutes at room temperature in a white 96 well plate for luminescent detection using a multimode microplate reader (Tecan Trading AG). Total protein concentration in the samples was measured using Micro BCA™ protein assay kit (Thermo Fisher, MA). Luminescence values were normalized by the total protein concentration of the supernatants.

Cryogenic Transmission Electron Microscopy (cryoTEM)

CryoTEM acquisition was performed on Glacios cryo-electron microscope equipped with Gatan K3 camera at 200 kV. 2 µl of the sample was dispensed on a plasma cleaned grid in the FEI Vitrobot chamber at 100% relative humidity and allowed to rest for 10 seconds. Then, the grid was blotted for 1 second with filter paper and plunged into liquid ethane cooled by liquid nitrogen. The frozen grids were then checked for visible defects and assembled into cassettes. The collected images were then processed and analyzed manually using Fiji. Each LNP population contained at least 85 particles. Only unobstructed LNP with clearly defined edges were included in the statistical analysis to ensure accurate representation of LNP populations and to avoid issues associated with ice thickness. The polydispersity index (PdI) was calculated as $PdI=(\sigma/\mu)^2$, where $\sigma$—standard deviation, and $\mu$—mean of particle size.

High-Temporal Resolution Single Particle Tracking

Three-dimensional trajectories of LNPs were collected using an active feedback tracking microscopy, 3D single-molecule active real-time tracking (3D-SMART). A 640 nm excitation laser (OBIS 640LX, Coherent, about 76 nW at the focus) was focused exclusively onto the sample through an objective lens (Zeiss Plan Apo, 100×, NA=1.49) and was deflected in a 1 µm×1 µm×2 µm 3D pattern by a pair of electro-optic deflectors (EODs; M310A, ConOptics) and a tunable acoustic gradient lens (TAG Lens 2.5, TAG Optics). Fluorescence photons from the moving probe are collected by the objective lens and are focused through a bandpass filter (ET706/95m, Chroma) onto a single-photon counting avalanche photodiode (Excelitas SPCM-ARQH-15). The photon arrival time was used to calculate the real-time 3D position of the moving probe within the laser scan using a field programmable gate array (NI-7852R) with a Kalman filter. The real-time position was then used to drive a galvo mirror (SG7220-A, Sino Galvo) and a piezoelectric nanopositioner (Z-Nano-OP65HS, MadCity Labs) to center the target in focal volume. All trajectories shown are sampled every 1 millisecond. To collect more trajectories and avoid uninterested stuck particles, the maximum trajectory time was set to 120 seconds, i.e., tracking will be automatically disengaged after collecting data for 120 seconds followed with a fresh round of searching process. Mucin suspensions were prepared as described. Briefly, native mucin from bovine submaxillary gland (Sigma-Aldrich, MO) was dissolved in distilled water at 10 mg/ml, followed by centrifugation at 10,000 g for 30 minutes to separate undissolved parts. The mucin-containing supernatant was lyophilized and resuspended in distilled water at 10 mg/ml. To quantify the diffusion, mean square displacement (MSD) analysis was applied to every trajectory longer than 5 seconds in duration. To keep consistent analysis, trajectories longer than 5 seconds in duration were broken up into 5 second segments, with a maximum of three segments (15 seconds) used for all trajectories. Diffusion coefficients extracted from different segments on the same particle were average together. The MSD was calculated as follows:

$$MSD(\tau) = N^{-1}\sum_{n=1}^{N}\left((x(n+\tau)-x(n))^2 + (y(n+\tau)-y(n))^2 + (z(n+\tau)-z(n))^2\right)$$

Here, $\tau$ is the lag time. $x(n)$, $y(n)$, and $z(n)$ are the coordinates of the trajectory at timepoint n. N is the total number of data points, 5000 for all segments analyzed in the present work. When available, the 95% confidence interval of the diffusion coefficient was calculated from the linear fit of $MSD(\tau)$ using the MATLAB (MathWorks) function confint. The alpha was calculated from the power law fit of $MSD(\tau)$.

$$MSD(\tau)=6D\tau^{\alpha}$$

To clean up the data, outliers were removed using the MATLAB function rmoutliers, in which an outlier is defined as a value more than three scaled median absolute deviations (MAD) away from the median. This acted to remove immobilized particles that were stuck to the coverslip during sample preparation.

Immunohistochemistry (IHC)

Ai9 mice (8-12 week old) were exposed to nebulized LNP encapsulating Cre recombinase mRNA for two days at a dose of 100 µg mRNA per day (3 mice per group). After 5 days, mice sedated by isoflurane were euthanized by cardiac puncture, and their hearts were perfused with sterile PBS through the right ventricle. Through the catheter inserted to the trachea, 4% paraformaldehyde (PFA) in PBS solution were instilled at 25 cm above the level of mouse to inflate the mouse lungs. After overnight incubation in 4% PFA, the inflated lungs were stored at 30% sucrose/PBS solution at 4° C. until the lungs sunk to the bottom of tubes. The lungs were embedded in the optimal cutting temperature (O.C.T) compound (Sakura Finetek USA, Inc., CA) and frozen using liquid nitrogen. The frozen sections were cut with 10 µm thickness on a cryostat. The sectioned tissues were permeabilized using 5% Triton X-200 in PBS for 10 minutes and blocked with 5% donkey serum in PBS for 1 hour. A primary antibody consisting of an anti-RFP antibody (1:100, rabbit, ab62341) in PBS containing 1% donkey serum covered the sections overnight at 4° C. The next day, the sections were washed with PBS and incubated in the secondary antibody (Donkey anti-rabbit Alexa Fluor Plus 647, 1:200, A32795, Thermo) in PBS containing 1% donkey serum for 1 hour at room temperature. The sections were washed with PBS, followed by nucleus staining and mounting with coverslips. Negative controls include the Cre mRNA treated lung sections stained with secondary antibody only and the untreated lung sections fully stained. Confocal images were obtained with the ZEISS LSM 880 (Carl Zeiss AG). Z-stacks (spanned 10 m with 1.08 m interval) were collected using a 20× objective, and maximum intensity projections were reported.

Histopathology and Serum Chemistry

BALB/c mice were exposed to nebulized PBS or LNP. After 24 hours, mice were euthanized, and the whole blood was collected by cardiac puncture. Serum was extracted from the whole blood samples using serum-separating tubes (BD). Afterward, mouse lungs were perfused with sterile PBS from the right ventricle. 20G catheter was inserted into the trachea to inflate lungs with 10% neutral buffered formalin (Fisher Scientific) at a pressure of 25 cm from the surgical plane. The inflated lungs were harvested and kept in formalin 24 hours. In the following days, the lungs were dissected, placed in tissue embedding cassettes, and submerged in 70% ethanol for dehydration. Tissues were paraffin embedded, sectioned, mounted on slides, routinely stained with hematoxylin and eosin, and cover-slipped allowing histopathologic evaluation by IDEXX BioAnalytics. Microscopic changes were graded as to severity utilizing a standard grading system whereby 0=no significant change, 1=minimal, 2=mild, 3=moderate, and 4=severe. International Harmonization of Nomenclature and Diagnostic (IN-HAND) Criteria standards are used as the basis of evaluation (www.toxpath.org/inhand.asp). Use of numerical grades allows a mechanism to calculate a total score lesion score which can be used to assess prevalence and severity of tissue changes within and between groups. Mouse sera were proceeded to clinical chemistry test by IDEXX BioAnalytics.

Pulmonary CFTR mRNA Transfection by LNP Inhalation

CFKO mice were exposed to nebulized LNP encapsulating Fluc or CFTR mRNA at a dose of 10 mg/kg/day for three days. At 48 hour after the last administration, mice were properly euthanized and lungs were collected. The lungs were homogenized with sterile PBS and centrifuged at 17,000 g for 30 minutes at 4° C. to collect supernatants, followed by supplementing protease and phosphatase inhibitor cocktail (Thermo Fisher, MA). Total protein concentration in the samples was measured using BCA™ protein assay kit (Thermo Fisher, MA). To detect CFTR protein, immunoprecipitation was performed. CFTR antibodies for pull-down and the following Western blot were an anti-CFTR mouse monoclonal antibody (596, Cystic Fibrosis Antibodies Distribution Program). Briefly, Dynabeads™ Protein G (Thermo Fisher, MA) were incubated with anti-CFTR antibodies at room temperature with rotation. The collected lung lysates containing 200 µg of total protein were incubated with the beads having anti-CFTR antibody with rotation. Following three washes with wash buffer, samples were eluted using elution buffer, denatured using LDS sample buffer and reducing agent at 37° C., and run on 8% Bis-Tris gels, followed by wet transfer to nitrocellulose membrane. The blots were blocked using 5% skim milk for 1 hour at room temperature. The primary antibodies used were anti-CFTR rabbit polyclonal antibody (HPA021939, Sigma-Aldrich, MO) at 1:1,000 and anti-α-Tubulin at 1:1,000 (Cell Signaling Technology, #2125). The secondary antibody was goat polyclonal anti-rabbit HRP (Jackson ImmunoResearch, 111-035-003) at 1:2,000 and 1:5,000 for CFTR and α-Tubulin, respectively. For detection and documentation, SuperSignal™ West Pico Plus Chemiluminescent Substrate and myECL imager were used (Thermo Fisher, MA). The Western blot images were analyzed using ImageJ (Version: 2.0.0).

Statistical Analysis

Statistical analysis was performed using Prism 9 software (GraphPad, CA, USA).

RESULTS

First, to test the influence of nebulization on LNP, an Onpattro® formulation was used, which is composed of DLin-MC3-DMA, 1,2-dimyristoyl-rac-glycerol-methoxy (poly(ethylene glycol)-2000 (DMG-PEG$_{2K}$), cholesterol, and 1,2-distearoyl-sn-glycero-3-phosphocholine (DSPC) at 50/1.5/38.5/10 molar ratios, respectively. The formulation was referred to as LNP-Chol/1.5. The dynamic light scattering (DLS) analysis showed that LNP-Chol/1.5 encapsulating Fluc mRNA (Onpattro® LNP) became larger, aggregated, and unstable in nebulization (FIG. 3). To make LNP stabler and smaller for nebulization, the amount of PEG lipid was varied, ranging from 1.5% to 7.5% (LNP-Chol/1.5-7.5; Table 1).

TABLE 1

Lipid molar compositions of various LNP formulations

| Formulation | Sterol | DSPC | DMG-PEG$_{2K}$ | DLin-MC3-DMA |
|---|---|---|---|---|
| LNP-Chol/1.5 (Onpattro ®) | Cholesterol, 38.5 | 10 | 1.5 | 50 |
| LNP-Chol/2.5 | Cholesterol, 38.5 | 9 | 2.5 | 50 |
| LNP-Chol/3.5 | Cholesterol, 38.5 | 8 | 3.5 | 50 |
| LNP-Chol/4.5 | Cholesterol, 38.5 | 7 | 4.5 | 50 |
| LNP-Chol/5.5 | Cholesterol, 38.5 | 6 | 5.5 | 50 |
| LNP-Chol/7.5 | Cholesterol, 38.5 | 5 | 7.5 | 50 |
| LNP-Sito/1.5 | β-sitosterol, 38.5 | 10 | 1.5 | 50 |
| LNP-Sito/2.5 | β-sitosterol, 38.5 | 9 | 2.5 | 50 |
| LNP-Sito/3.5 | β-sitosterol, 38.5 | 8 | 3.5 | 50 |
| LNP-Sito/4.5 | β-sitosterol, 38.5 | 7 | 4.5 | 50 |

Figure 4:
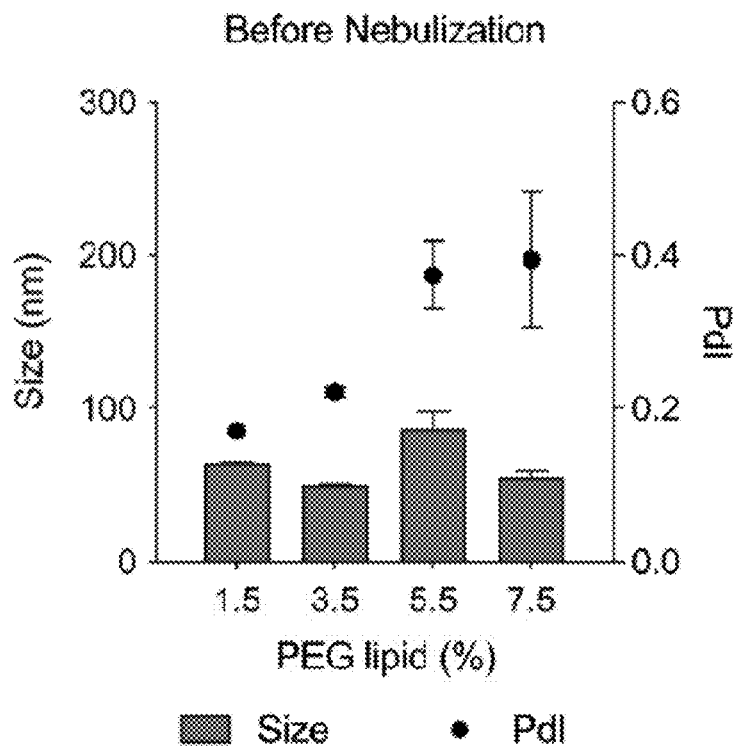
Figure 5:
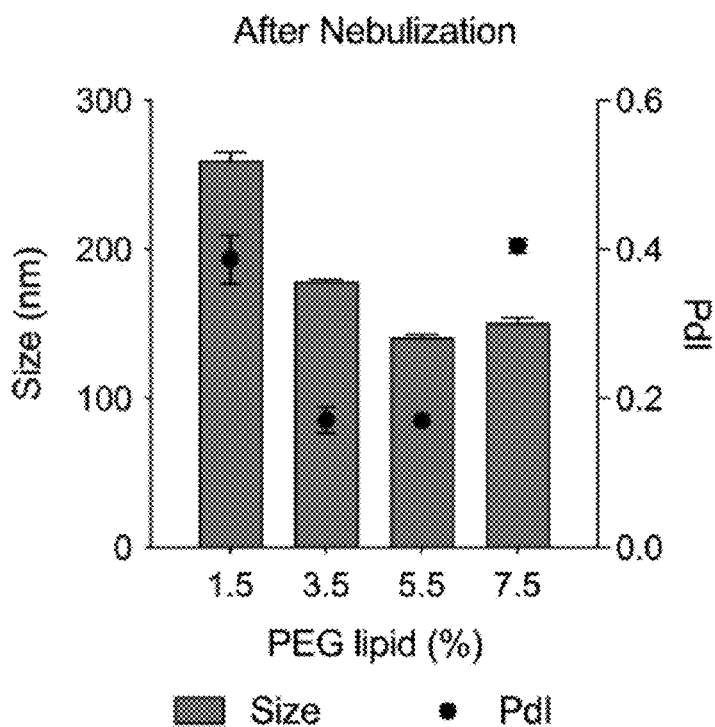
Figure 6:
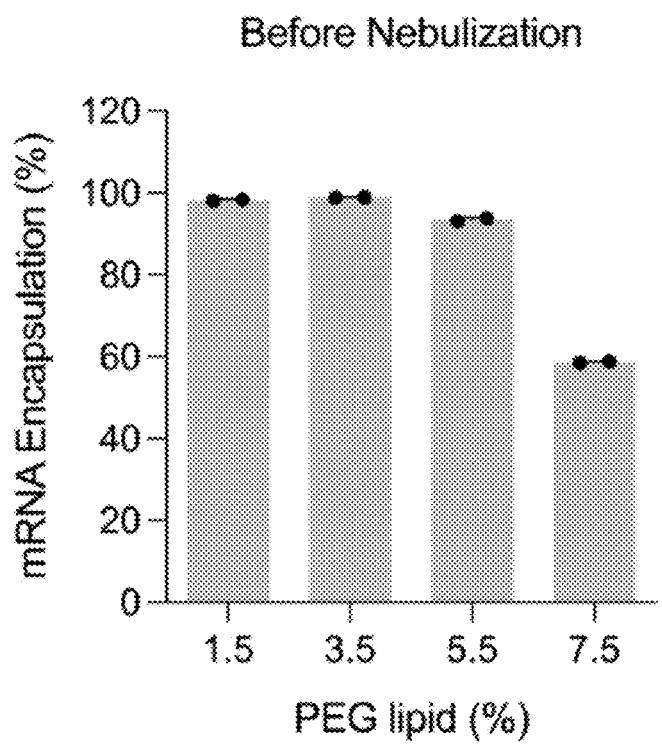
Figure 7:
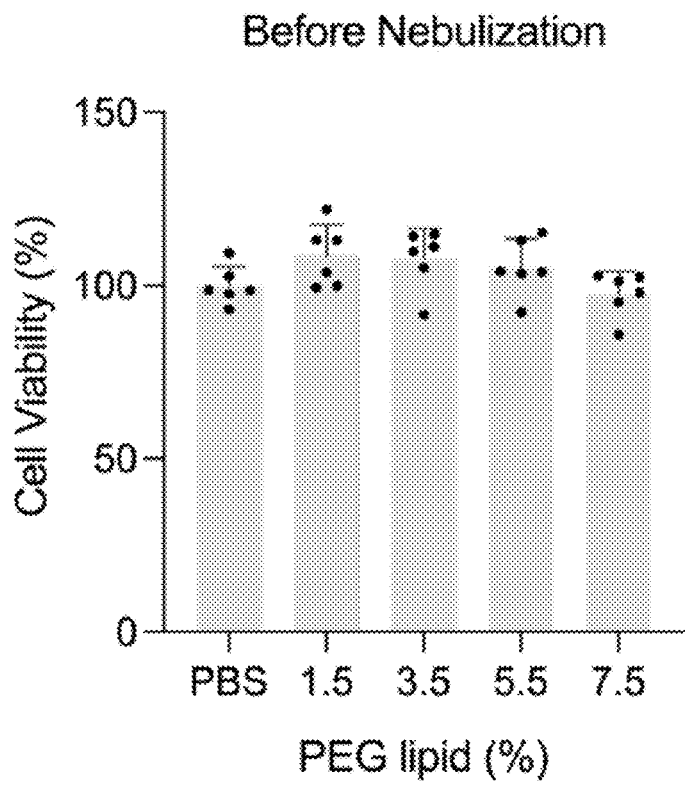
Figure 8:
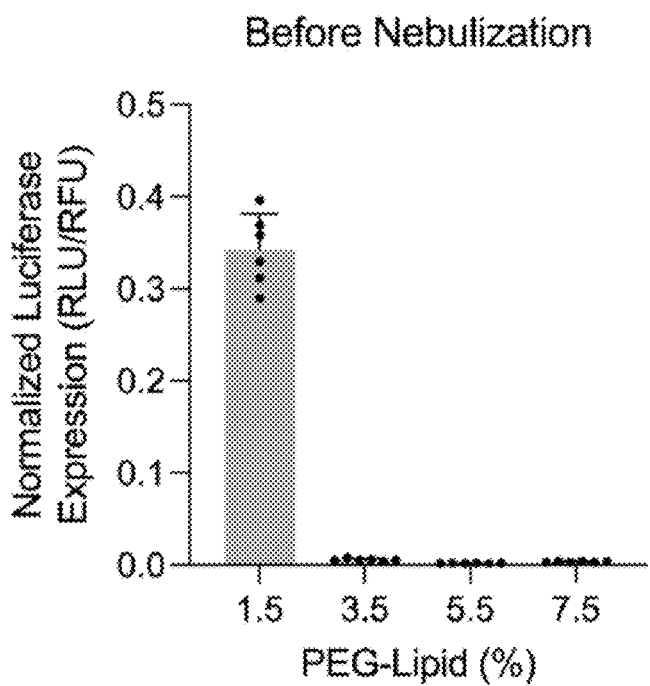

Increasing PEG lipid from 1.5% to 3.5% (LNP-Chol/1.5 vs. LNP-Chol/3.5) led to a decrease in LNP size. However, LNP-Chol/5.5 and LNP-Chol/7.5 exhibited a relatively larger size and polydispersity index (PdI), suggestive of the destabilization of the LNP containing PEG lipid more than 5.5% (FIG. 4). After nebulization, LNP-Chol/1.5 exhibited the larger size and PdI than the LNP with more PEG lipid (FIG. 5), which suggested that having high PEG contents helped the LNP be more resistant to shear stress. mRNA encapsulation appeared to decrease in LNP-Chol/5.5, suggesting that having excessive PEG lipid might be detrimental to the RNA encapsulation (FIG. 6). Increasing PEG lipid in LNP did not appear cytotoxic to HeLa cells (FIG. 7) but it significantly deprived LNP of the ability to transfect cells (FIG. 8), which could be due to the excessive PEG inhibiting the endocytosis.

To overcome the loss of transfection derived from high PEG contents, cholesterol derivatives were used. LNPs using β-sitosterol in place of cholesterol were prepared, and it was hypothesized that a combination of β-sitosterol and high PEG contents could enable LNP to be stable enough for nebulization and penetrate mucosal barriers while effectively delivering mRNA to cells.

Cholesterol

β-sitosterol

Figure 9:
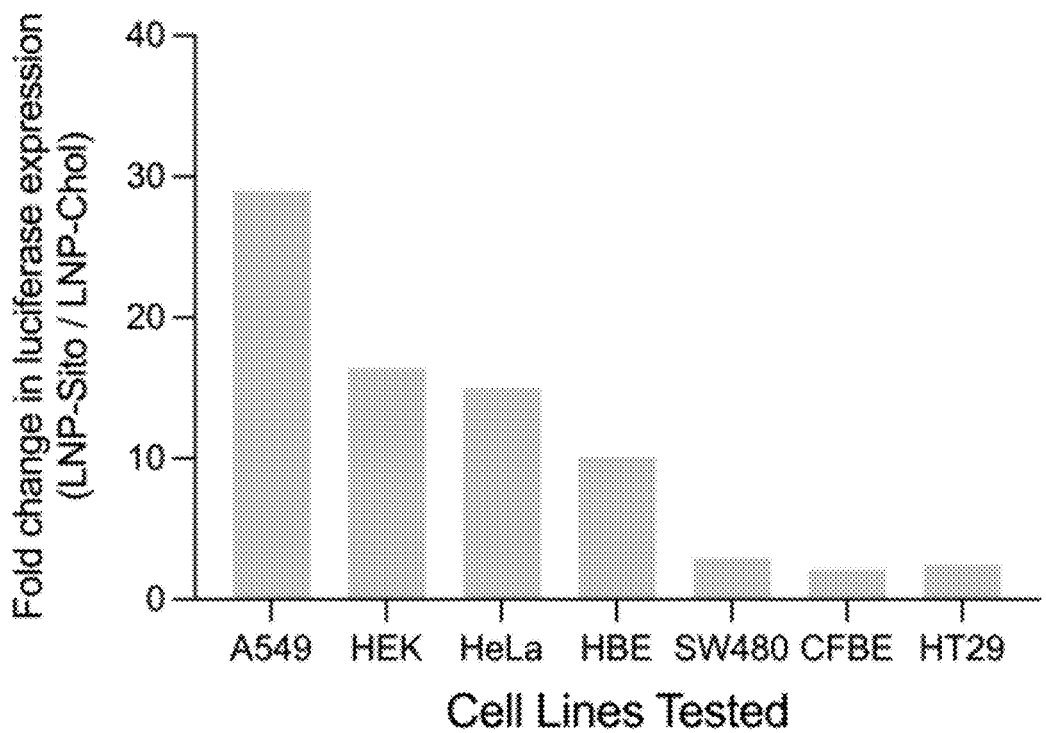
Figure 10:
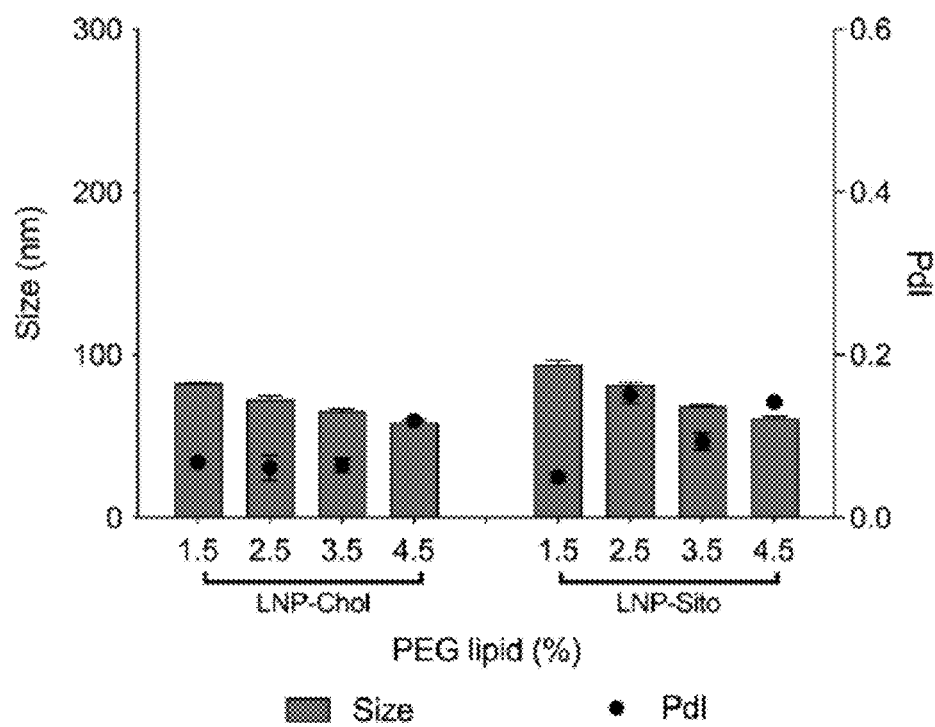
Figure 11:
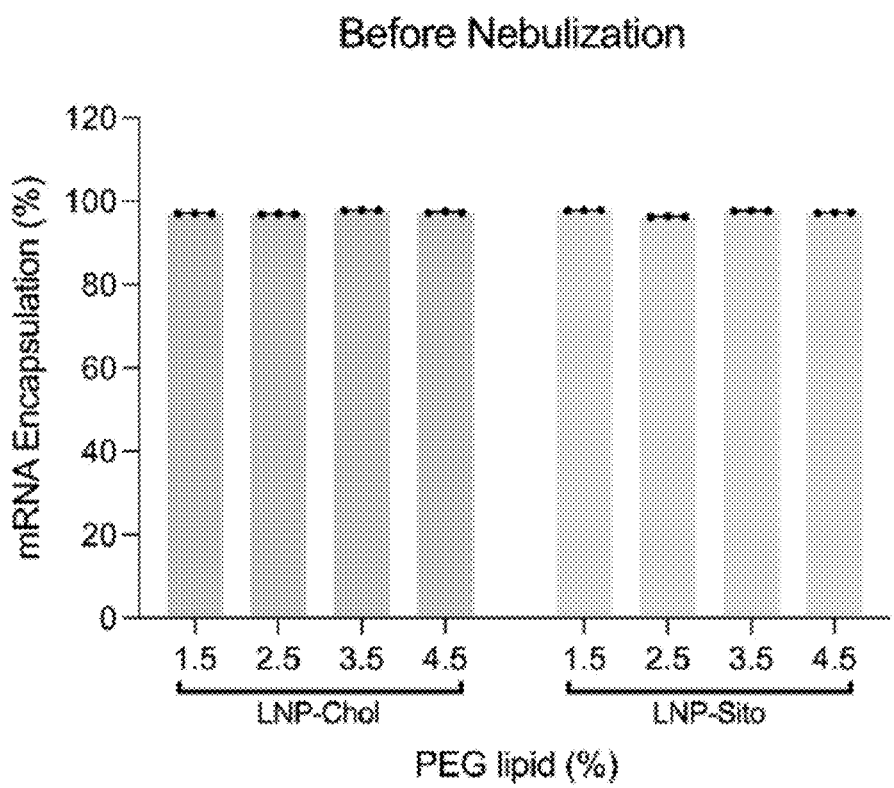
Figure 12:
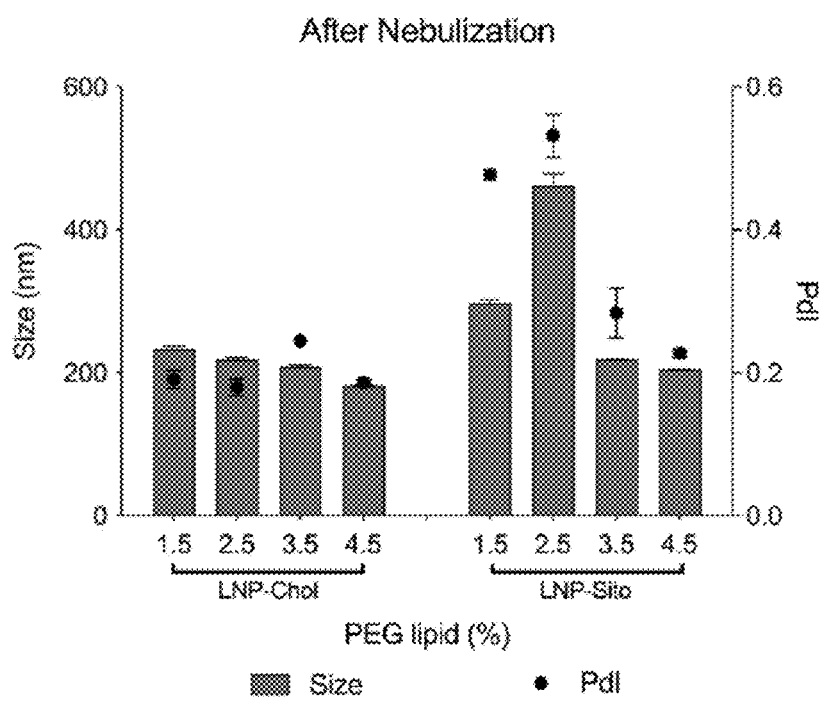
Figure 13:
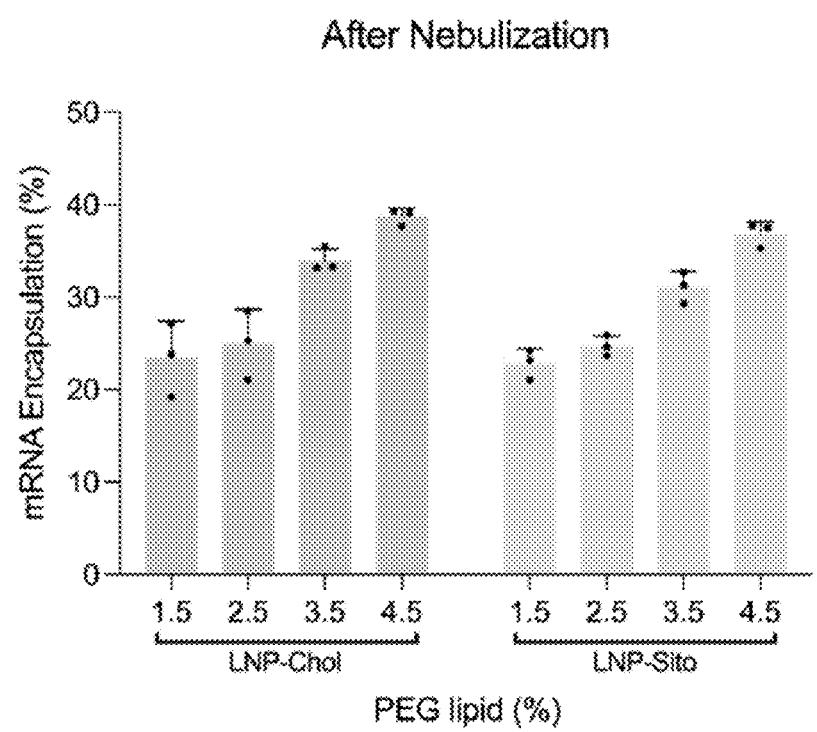
FIG. 13 is a graph of mRNA encapsulation versus percentage of PEG lipid, illustrating the percentage of mRNA encapsulation of LNP-Chol and LNP-Sito containing various amounts of PEG lipid after nebulization.
Figure 14:
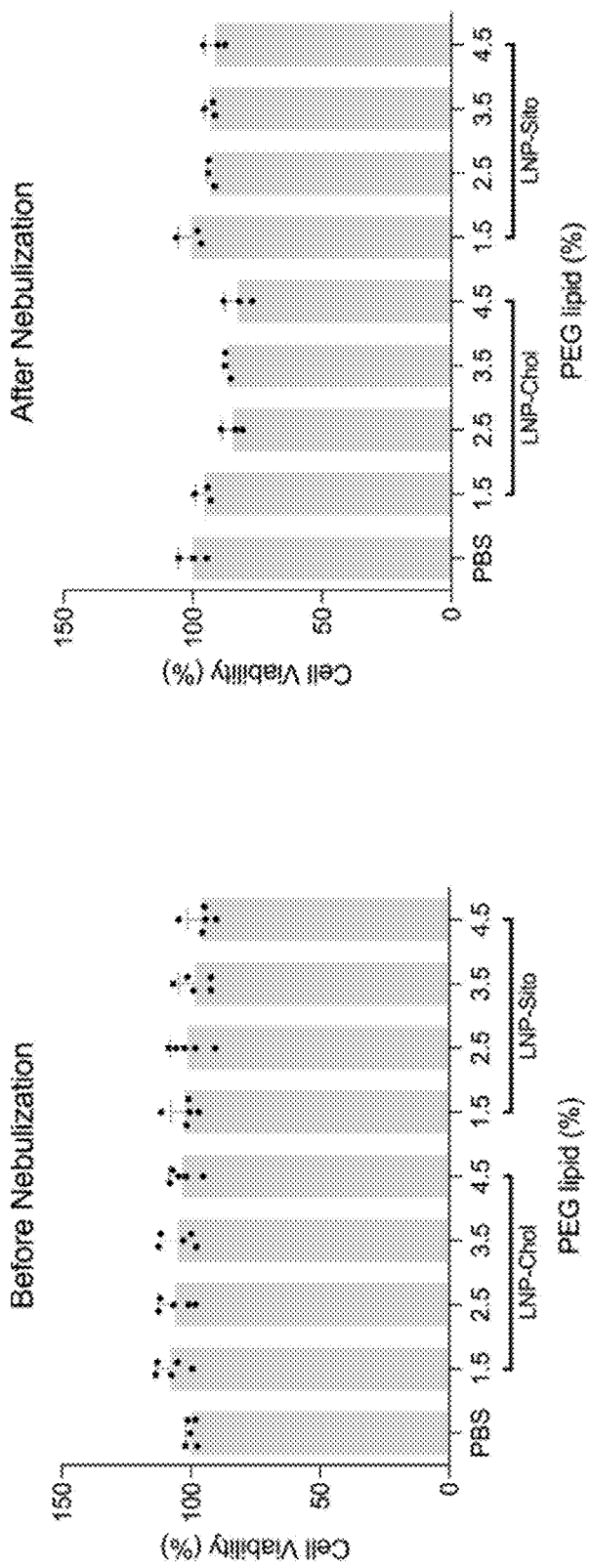
FIG. 14 are graphs of cell viability versus percentage of PEG lipid, illustrating the in vitro cell viability of HeLa cells treated with LNP solution at a dose of 50 ng/well, or nebulized LNP at a dose of 1 μg Fluc mRNA per well for 24 hours.
Figure 15:
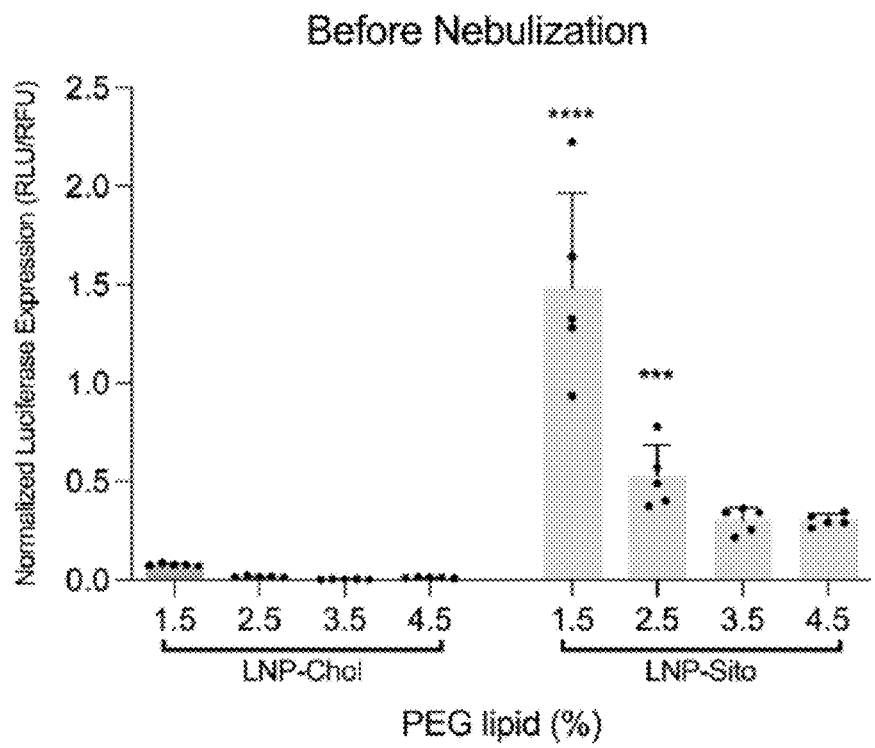
FIG. 15 is a graph of normalized luciferase expression versus percentage of PEG lipid, illustrating the luciferase expression in HeLa cells transfected with LNP solution at 50 ng and 1 μg mRNA per well.
Figure 16:
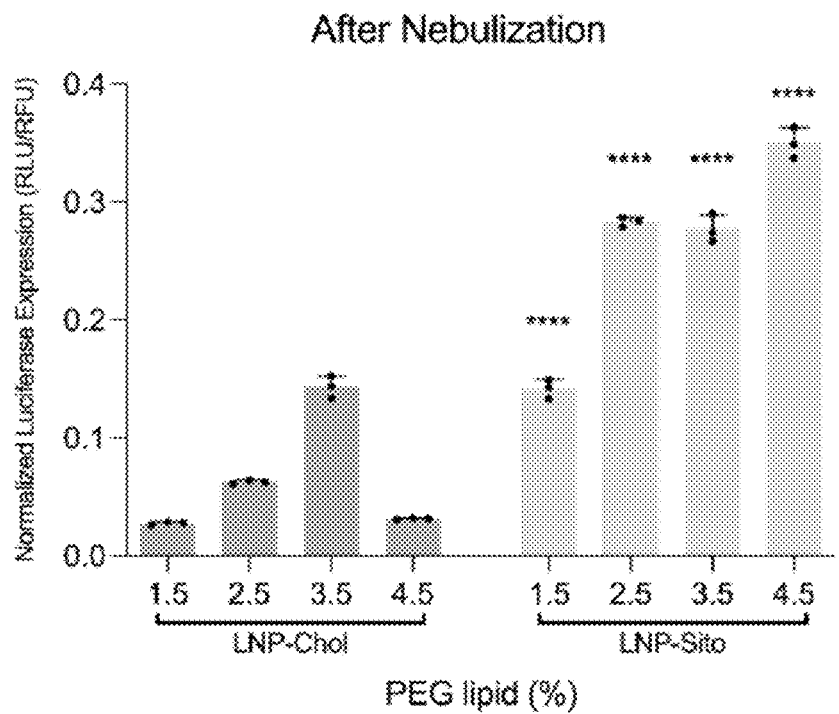
FIG. 16 is a graph of normalized luciferase expression versus percentage of PEG lipid, illustrating the luciferase expression in HeLa cells transfected with LNP aerosol at 50 ng and 1 μg mRNA per well.
Figure 17:
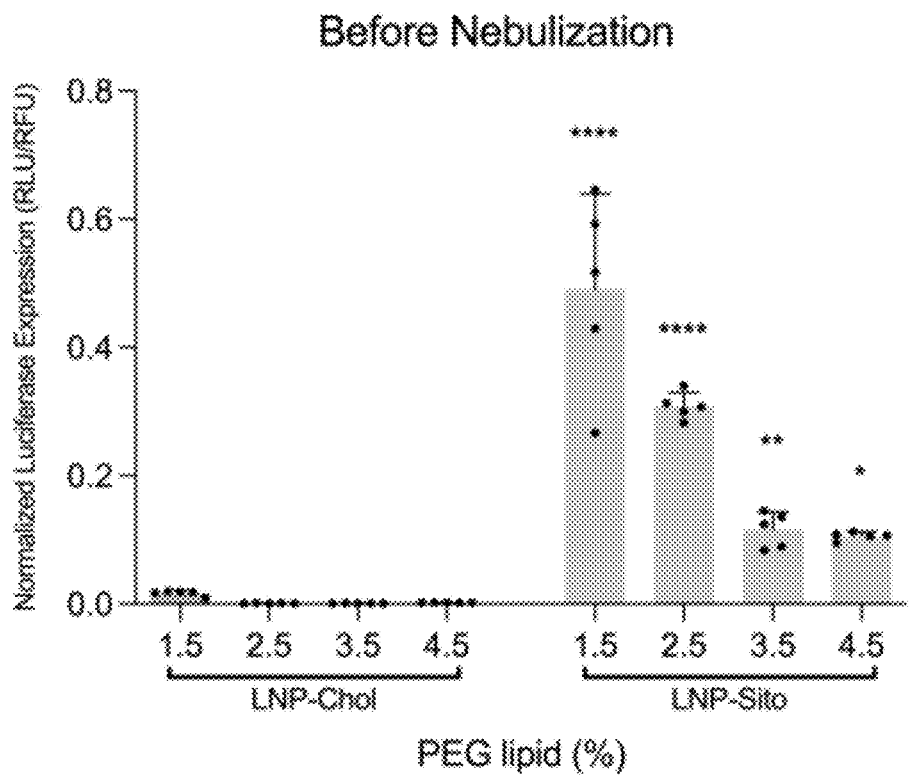
FIG. 17 is a graph of normalized luciferase expression versus percentage of PEG lipid, illustrating the luciferase expression of A549 cells treated with LNP solution at a dose of 50 ng Fluc mRNA per well.
Figure 18:
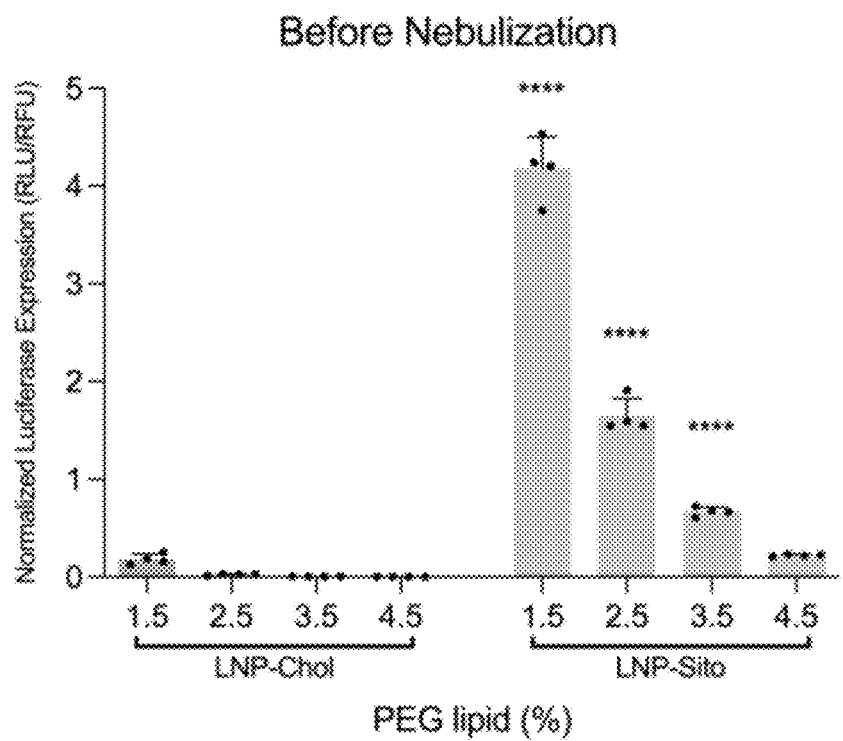
FIG. 18 is a graph of normalized luciferase expression versus percentage of PEG lipid, illustrating the luciferase expression of 16HBE14o-cells treated with LNP solution at a dose of 200 ng Fluc mRNA per well.
Figure 19:
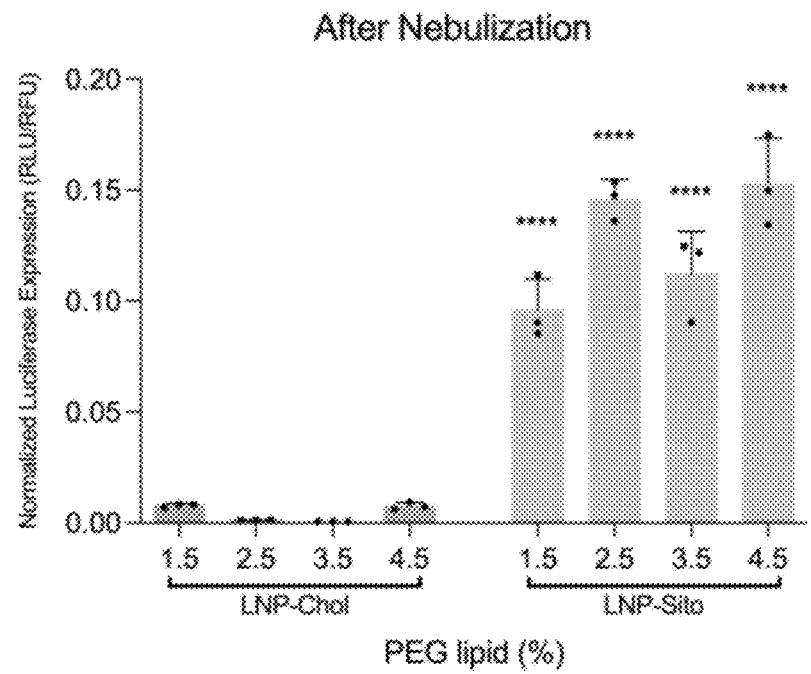
FIG. 19 is a graph of normalized luciferase expression versus percentage of PEG lipid, illustrating the luciferase expression of A549 cells treated with LNP aerosol at a dose of 1000 ng Fluc mRNA per well.
Figure 20:
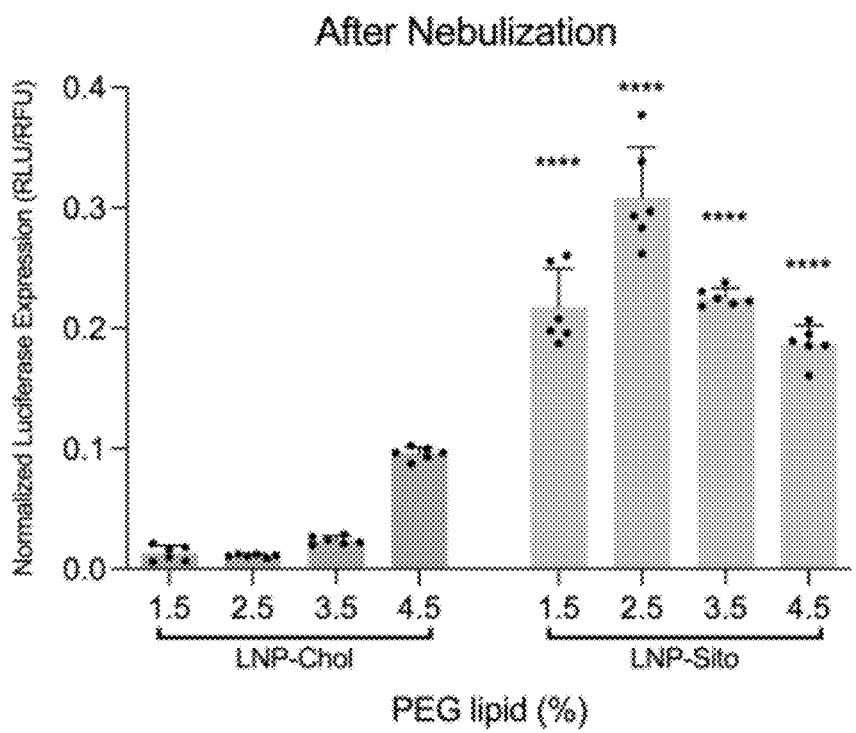
FIG. 20 is a graph of normalized luciferase expression versus percentage of PEG lipid, illustrating the luciferase expression of 16HBE14o-cells treated with LNP aerosol at a dose of 500 ng Fluc mRNA per well.

To verify the effects of sterol substitution, LNP containing cholesterol (LNP-Chol/1.5) and β-sitosterol (LNP-Sito/1.5) were prepared and tested in an array of human cell lines, including several lung epithelial cell lines: A549, 16HBE14o-, and CFBE. LNP-Sito/1.5 delivered Fluc mRNA more efficiently than LNP-Chol/1.5 in all cell lines tested (FIG. 9). To evaluate if the substitution of β-sitosterol in place of cholesterol in LNP could offset the loss of transfection received from high PEG contents, the effects of the PEG contents in LNP-Chol and LNP-Sito were tested, ranging from 1.5% to 4.5% of PEG lipid (Table 1). It was shown that LNP size decreased in response to the increasing PEG contents (FIG. 10), and all LNP formulations displayed high mRNA encapsulations (>90%) prior to nebulization (FIG. 11).

After nebulization, LNP-Chol/1.5-4.5 showed modest increases in size and PdI. Nebulized LNP-Sito/1.5 and LNP-Sito/2.5 exhibited notable increases in size and PdI; however, LNP-Sito/3.5 and LNP-Sito/4.5 displayed similar values in size and PdI as compared to LNP-Chol/3.5 and LNP-Chol/4.5 (FIG. 12). It might indicate that the level of PEG lipid to inhibit LNP-Sito from aggregation during nebulization is around 3.5%. mRNA encapsulation within LNP decreased after nebulization (FIG. 13). It likely represents the leakage of the encapsulated mRNA to the outside of LNP caused by the rearrangement of the LNP structure during nebulization. Although all nebulized LNP exhibited lower than 50% RNA encapsulation, having relatively high PEG contents appeared to retain mRNA better within nebulized LNP during nebulization (FIG. 13). In vitro transfection assay in HeLa cells revealed that LNP-Chol and LNP-Sito both caused negligible cytotoxicity regardless of nebulization (FIG. 14). In the following luciferase assay in HeLa cells, surprisingly LNP-Sito showed significantly greater Fluc mRNA transfection than LNP-Chol in all various PEG lipid contents (FIG. 15). Both LNP-Chol and LNP-Sito exhibited decreasing luciferase expression when PEG lipid percentages increased, and LNP-Sito/1.5 led to the highest luciferase expression among all tested formulation (FIG. 15). Notably, mRNA transfection by nebulized LNP was different by showing that LNP-Sito containing relatively high PEG contents outperformed the one containing low PEG contents (FIG. 16). Luciferase expressions of nebulized LNP-Sito were constantly higher than those of nebulized LNP-Chol. Especially, LNP-Sito with 4.5% PEG resulted in a higher luciferase expression than all other LNP, 12-fold greater than LNP-Chol/1.5 (Onpattro® formulation; FIG. 16). The LNP library was further tested in two lung epithelial cell lines: A549 and 16HBE14o-. Likewise, LNP-Sito showed higher transfection than LNP-Chol in both cells with decreasing potencies in response to increasing PEG lipid contents (FIGS. 17 and 18). After nebulization, LNP-Sito similarly produced higher luciferase expressions than LNP-Chol (FIGS. 19 and 20). Unlike HeLa cells, the effects of PEG lipids in the mRNA transfection of LNP-Sito were less noticeable in A549 and 16HBE14o-cells (FIGS. 19 and 20). Summarizing in vitro results, LNP-Sito containing high PEG lipid contents are capable of delivering mRNA to the cells effectively while preventing particles from aggregation.

Next, investigations were performed to determine whether varying PEG lipid contents affects LNP morphology using cryogenic transmission electron microscopy (cryoTEM). LNP-Chol produced uni-lamellar shapes, and LNP-Sito showed polymorphic, polyhedral, multi-lamellar shapes (FIGS. 21 and 22). Moreover, altering PEG lipid contents changed the particle size. Size comparison of LNP by cryoTEM and DLS showed a similar trend: increasing PEG lipid contents decreased the particle size.

TABLE 2

Size measurement of LNP-Chol and LNP-Sito containing various PEG-lipid content in DLS and CryoEM

| % DMG- | DLS | | CryoEM | |
|---|---|---|---|---|
| $PEG_{2K}$ | LNP-Chol | LNP-Sito | LNP-Chol | LNP-Sito |
| 1.5% | 82.79 ± 0.79 nm | 94.10 ± 2.49 nm | 50 ± 10 nm | 70 ± 15 nm |
| 2.5% | 72.95 ± 2.00 nm | 81.68 ± 1.90 nm | 56 ± 15 nm | 60 ± 8 nm |
| 3.5% | 65.20 ± 1.58 nm | 68.46 ± 0.62 nm | 41 ± 6 nm | 43 ± 8 nm |
| 4.5% | 58.52 ± 1.37 nm | 60.98 ± 1.05 nm | 33 ± 8 nm | 33 ± 11 nm |

Data is presented as mean ± standard deviation. (DLS; n = 3, CryoEM; n = 5-20)

Both methods consistently revealed that, at the same concentration of PEG lipid incorporated, LNP-Chol were smaller than LNP-Sito. While the particle size varied depending on PEG lipid contents, polyhedral shapes of LNP-Sito remained. This size difference was more pronounced in cryoTEM results due to the low contrast of PEG layers in the micrographs (Table 2). When PEG lipid was included at greater than or equal to 3.5%, LNP size became comparable between LNP-Chol and LNP-Sito (Table 2). It was shown that anisotropy of LNP-Chol was higher than that of LNP-Sito, indicative of influence of sterol substitution on lipid membrane rigidity. Considering the different morphology, size, and membrane rigidity of LNP-Chol and LNP-Sito, these structural and morphological features may have led to the rearrangement of the nanoparticles at different degrees when exposed to nebulization, which could have contributed to the transfection.

Having confirmed the potential advantages of combining β-sitosterol and a high PEG content for LNP nebulization, evaluations continued in vivo. The aerosol exposure system was used to connect a rodent restraint to a vibrating mesh nebulizer via a spacer so that nebulized LNP could reach the mouse nose by laminar flow of medical-grade compressed air (FIG. 23). This system enables the effective administration of LNP at a relatively low dose compared to a whole-body nebulization chamber. Further, nanoluciferase (Nluc) mRNA was used instead of Fluc mRNA because Nluc emits brighter signals than Fluc, which increased the signal-to-noise ratio of bioluminescence upon mRNA transfection. The synthesized Nluc mRNA showed approximately 800 nucleotides in length under the agarose gel electrophoresis (FIG. 24). LNP-Chol and LNP-Sito containing Nluc mRNA and various PEG lipid contents were nebulized at a dose of 100 μg Nluc mRNA per mouse and measured luminescence in collected mouse lungs 24 hours after nebulization (FIG. 23). Ex vivo imaging results proved that nebulized LNP transfected the lungs (FIG. 25). Of note, no other organs (including the liver) showed any luciferase expression after inhalation of nebulized LNP, indicating that LNP inhalation offers the selective transfection of the lungs (FIG. 25). Additionally, luciferase expression was detected in all five lung lobes, suggesting that nebulized LNP travel through airways evenly (FIGS. 26 and 27). The difference in luciferase expression detected in each lung lobe was insignificant (p>0.5; FIG. 27). Luminescent signals were further measured in the lung homogenates using a luminometer to assay luciferase transfection, followed by normalization against total protein concentrations. As a result, inhalation of LNP-Sito led to higher luciferase expression than LNP-Chol at 1.5%, 2.5%, and 3.5% of the PEG lipid included (FIG. 28). LNP-Sito produced significantly higher luciferase expressions than LNP-Chol when 1.5 and 3.5% PEG lipid were used (FIG. 28). LNP-Chol/4.5 and LNP-Sito/4.5 led to the comparable luciferase expressions. LNP-Chol exhibited relatively consistent despite the various amounts of PEG lipid (FIG. 28).

To further optimize LNP for inhalation, the nanoparticle mobility in a glycoprotein-rich condition was evaluated. Airway mucus, a viscoelastic matrix in which water and mucin are the primary components, is secreted by secretory cells and submucosal glands. A porcine mucin suspension was used to mimic mucosal barriers against inhaled nanoparticles. To compare the diffusivity of LNP-Sito with different PEG-lipid contents in mucin suspension, three-dimensional (3D) Single-Molecule Active Real-time Tracking (3D-SMART) was employed to measure the diffusion of individual nanoparticles. Two formulations, LNP-Sito/1.5 and LNP-Sito/3.5, encapsulating Cy5-labelled EGFP-mRNA were added to a 10 mg/mL mucin suspension. 3D-SMART was used to capture the three-dimensional motion of individual nanoparticles within these mixtures for about 4 hours. Representative trajectories of LNP-Sito/1.5 and LNP-Sito/3.5 in 10 mg/mL mucin suspension were visualized (FIG. 29). Mean square displacement (MSD) analysis was performed on each trajectory and the diffusion coefficient and alpha were calculated for both formulations (LNP-Sito/1.5: n=323; LNP-Sito/3.5, n=353). The alpha values, which indicates the linearity of the MSD curve, were less than 1 for both formulations, but there was no significant difference between the two test groups (p=0.34, FIG. 30). This indicates that both formulations showed a small amount of sub-diffusive character in mucin suspension, but that the degree of sub-diffusions is not affected by the concentration of PEG lipid. Despite the similar alpha values, analysis of the diffusion coefficients of individual particles in mucin suspensions revealed that a relatively small addition of PEG lipid contents to LNP dramatically expands the travel ranges of the nanoparticles in a mucin suspension (FIG. 31 left). Precisely, LNP-Sito/1.5 (1.69±0.81 μm$^2$/s) was significantly less diffusive than LNP-Sito/3.5 (3.11±1.66 μm$^2$/s, p<0.0001) in a mucin suspension (FIG. 31 right). This enhancement in diffusivity could be explained by the fact that the PEG reduces the affinity of the LNP for mucins, which could facilitate the delivery process across mucosal barriers. Consequently, LNP-Sito/3.5 was selected as the optimized formulation for further inhalation studies based on its physicochemical properties, mucosal mobility, and in vivo efficacy, and named it nebulizable LNP (nLNP).

To determine the extent of mRNA delivery throughout the lungs using nLNP, the tissue-specific gene expression in the lungs was studied using Ai9 tdTomato reporter mouse that exhibits tdTomato protein expression after Cre-Lox recombination (FIG. 32). nLNP was prepared with encapsulating Cre mRNA and administered to Ai9 mice via inhalation, followed by five-day incubation for the site-specific recombination. In the lung sections of the Ai9 mice exposed to LNP inhalation, tdTomato expression was detected in alveoli and respiratory bronchioles, suggesting that inhaled LNP accumulate to a wide range of the bronchial tree. (FIGS. 33 and 34). In the lung sections of untreated Ai9 mouse, tdTomato expression was insignificant (FIG. 35).

Next, acute adverse effects of nLNP inhalation to BALB/c mice were tested using clinical chemistry and histopathology. In the clinical chemistry test, the overall results of the LNP-treated group were similar to those of the PBS-treated group, suggesting the safety of inhalation nLNP (FIGS. 36 and 37 and Table 3). Total protein concentration was significantly higher in nLNP-treated group than PBS-treated group; however, the mean value was still within the normal range of BALB/c mouse (FIG. 36 and Table 3). The elevation of blood aspartate aminotransferase (AST) of nLNP-treated group was insignificant when compared to the level of PBS-treated group (p=0.4; FIG. 37 and Table 3).

TABLE 3

Results of clinical chemistry of mouse sera collected after inhalation exposure

| | Results | |
|---|---|---|
| Parameter | PBS-treated | LNP-treated |
| ALP (U/L) | 100.7 ± 7.2 | 107.3 ± 8.1 |
| AST (U/L) | 44.7 ± 5.5 | 62.3 ± 34.6 |
| ALT (U/L) | 19.3 ± 2.1 | 22.3 ± 5.9 |
| GGT (U/L) | 0.0 ± 0.0 | 0.0 ± 0.0 |
| Albumin (g/dL) | 2.7 ± 0.0 | 2.8 ± 0.1 |
| Total Bilirubin (mg/dL) | 0.2 ± 0.1 | 0.1 ± 0.1 |
| Total Protein (g/dL) | 4.2 ± 0.1 | 4.5 ± 0.1 |
| Globulin (g/dL) | 1.5 ± 0.1 | 1.7 ± 0.1 |
| BUN (mg/dL) | 22.0 ± 2.6 | 22.0 ± 2.6 |
| Creatinine (mg/dL) | 0.1 ± 0.1 | 0.1 ± 0.0 |
| BUN/Creatinine Ratio | 150.0 ± 132.3 | 220. ± 26.5 |

The potential acute lung damage after nLNP inhalation was further evaluated by histopathology (FIG. 38). In the histopathological analysis of the lung sections exposed to PBS or nLNP, the lungs from both groups were mildly atelectatic (FIG. 39 and Table 4). Focal, small clots of mononuclear cells, fibrin, and scattered erythrocytes were found in both vehicle and LNP treated lungs. Clots are found adjacent to pleura, within small vessels, or in alveolar ducts. The finding is considered to most likely be incidental and unrelated to treatment. However, no significant difference was observed between the two groups, indicating that the abnormalities are artefactual findings and not treatment-related (FIG. 38 and Table 4).

TABLE 4

Summary of Histopathological Findings

| | PBS-treated | | | LNP-treated | | |
|---|---|---|---|---|---|---|
| Parameter | # Abnormal | Mean Group Score | Mean Lesion Score | # Abnormal | Mean Group Score | Mean Lesion Score |
| Congestion | 0 | 0 | | 1 | 0.7 | 2 |
| Mononuclear clot/aggregate | 1 | 0.3 | 1 | 3 | 1 | 1 |
| Artifact | 3 | 2 | 2 | 3 | 2 | 2 |
| Sum-Scores: | 1 | 0.3 | 1 | 4 | 1.7 | 3 |
| No Significant Findings | 2 | | | 0 | | |

The transient nature of mRNA therapeutic allows for the controllable expression of the target protein; however, persistent administration is necessary to maintain the protein expression within the therapeutic window. Accordingly, tests were performed to determine whether the optimized LNP can be given repeatedly (FIG. 40). nLNP was administered via inhalation every 3 days at a dose of 5 mg/kg/day mRNA (FIG. 40, top arrows). At 24 hours after each dose, mouse lungs were collected to measure luciferase expression (FIG. 40, bottom arrows). Throughout three measurements of luciferase expression post-inhalation, the Nluc expression levels were maintained (FIGS. 41-43). The body weight changes of the animals were also insignificant during the study (FIG. 44). These results demonstrated that single- or repeated-inhalation of nLNP did not pose any risk of acute toxicity in vivo.

Lastly, human CFTR (hCFTR) mRNA was delivered using nLNP to test whether nLNP can deliver therapeutic mRNA (FIG. 45). nLNP encapsulating CFTR or Fluc mRNA was administered to CFKO mice daily for 3 days, as illustrated by the arrows at day 0, 1 and 2, followed by harvesting lungs to detect CFTR proteins on day 4. To study the expression of hCFTR protein, a well-characterized bitransgenic CFKO mouse model was used. This mouse model is fully knocked out for the endogenous mouse CFTR. Three doses of mRNA were given to the CFKO mouse model via inhalation, followed by collecting lungs to detect hCFTR. During the treatment, no significant change in the body weight of CFKO mice was observed (FIG. 46). An immunoprecipitation (IP) approach was performed to examine the presence of hCFTR protein in the lungs of CFKO mice after mRNA inhalation. The IP revealed the presence of hCFTR protein at approximately 170 kDa in the precipitated samples of the CFKO mice treated with CFTR mRNA inhalation (FIG. 47). mRNA delivered by nLNP is noted above the images. Upper and lower blots were probed using anti-CFTR and anti-α-Tubulin antibodies, respectively, and approximate molecular weights are marked on the left sides of the images.

In the precipitated samples of the CFKO mice treated with Fluc mRNA inhalation, the expression of hCFTR protein was not detected (FIG. 47). α-Tubulin bands were detected in the flow-through samples of both groups (FIG. 47). These data indicated that hCFTR mRNA delivered by nLNP produced hCFTR protein in the mouse lungs. Non-specific bands were also found in the blots of the precipitated samples (FIGS. 48 and 49). After inhalation of nLNP encapsulating hCFTR or Fluc mRNA, the CFKO mouse lungs were harvested, homogenized, and lysated for the IP and Western blot (FIG. 48). With respect to FIG. 48, the boxes marked with dashed lines indicate: for IP-hCFTR protein (top), the hCFTR antibody (top middle), and heavy chains (lower middle) and light chains (bottom) of the antibody; and for FT, the marked box indicates α-Tubulin. IP with PBS was performed as a control (FIG. 49). With respect to FIG. 49, the marked boxes indicate the hCFTR antibody (top), and heavy chains (middle) and light chains (bottom) of the antibody.

Considering that the same bands were observed when we conducted the IP with PBS, they seemed to be the anti-CFTR antibody and its heavy and light chains (FIG. 49). Taken together, the results demonstrate that CFTR mRNA can be delivered using inhalation of nLNP to the lungs for the potential treatment of cystic fibrosis.

DISCUSSION AND CONCLUSIONS

Extrahepatic delivery of therapeutic mRNA via LNP paves the way for the treatment of diseases unrelated to the liver. The lungs are associated with various diseases, including inherited genetic disorders, cancers, and infectious diseases. Nevertheless, pulmonary delivery of mRNA is a difficult task since many nanoparticles preferentially accumulate to the liver when administered systemically. Furthermore, lipid-based vectors are particularly challenging to move beyond the liver because of strong interactions with apolipoprotein E (ApoE), leading to the low-density-lipoprotein (LDL) receptor-mediated cellular uptake to the hepatocytes. Therefore, inhalation route is of interest for pulmonary delivery of mRNA.

Polymeric nanoparticles have the advantage of self-assembling with mRNA, which could be advantageous to recover nanostructures after being nebulized. However, it is challenging to synthesize monodispersed polymers on an industrial scale, and the positive charges in cationic polymers often lead to cytotoxicity. In contrast, LNP are considered more potent and tolerant than polymeric nanoparticles. Additionally, the manufacturing capabilities of mRNA vaccines will also enable the large-scale production of LNP-based mRNA therapeutics. To date, LNP chemistry has been optimized mainly for intravenous or intramuscular administrations. However, it is not readily translatable for inhalation due to the different requirements for compatibility with inhalation devices and the unique characteristics of the respiratory system, such as its anatomical structure and the existence of mucosal barriers. Therefore, the formulation criteria for LNP inhalation are likely different to those for other administration routes.

This study has explored the design criteria for LNP nebulization with the clinically relevant ionizable lipid, DLin-MC3-DMA. The molar percentage of PEG lipid among lipid components was used to control the LNP size after nebulization. However, it was also found that excess PEG lipid could be disadvantageous for mRNA transfection. Dense PEG could inhibit the formation of biomolecular corona on the nanoparticles, thus negatively affecting the cellular entry of nanoparticles. As ApoE assists the LNP uptake in the systemic circulation, potential facilitators could exist in the airway surface liquid for LNP uptake. In the pulmonary system, alveolar macrophages abundantly produce ApoE, and lung epithelial cells express LDL receptors. Therefore, if ApoE assists LNP uptake in the lungs in the same way it does in the systemic circulation, the restricted interactions between heavily PEGylated LNP and ApoE would diminish the cellular uptake of LNP and the resulting mRNA transfection.

To overcome this double-edged effect of PEG lipid in LNP nebulization, a small library of LNP formulations was explored and the disclosed LNP were identified for inhalation-mediated mRNA delivery to the lungs. The disclosed LNP contain cholesterol derivatives, such as β-sitosterol, and also have high PEG lipid contents, and were resilient to shear stresses during nebulization. In addition, 3D-SMART revealed that the disclosed LNP displayed the superior diffusivity in mucin suspension at single-nanoparticle resolution. This feature can be useful to treat the lung diseases characterized with hypersecretion and impaired clearance of sputum; for example, asthma, chronic obstructive pulmonary disease, and cystic fibrosis. Considering that airway mucus is an important factor stopping LNP from transfecting epithelial cells, LNP having high diffusivity would enhance the chance of traversing mucosal barriers and reaching airway epithelium. Inhaled nLNP also provided effective mRNA transfection in mouse epithelial cells without off-target transfection in the liver. Furthermore, they did not induce any significant change in serum toxicology tests as well as histopathology, supporting its safety.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A nanoparticle comprising:
   from 30 mol % to 65 mol % of an ionizable lipid;
   from 30 mol % to 60 mol % of β-sitosterol;
   from 5 mol % to 20 mol % of a structural lipid; and
   from 3.5 mol % to 4.5 mol % of a PEG lipid;
   in amounts relative to each other.

2. The nanoparticle of claim 1, wherein the nanoparticle comprises:
   from 45 mol % to 55 mol % of the ionizable lipid; or
   from 37 mol % to 40 mol % of the β-sitosterol; or
   from 9 mol % to 10 mol % of the structural lipid; or
   any combination thereof.

3. The nanoparticle of claim 1, wherein the ionizable lipid is DLin-MC3-DMA, 1-Linoleoyl-2-linoleyloxy-3-dimethylaminopropane (DLin-2-DMAP), 1,2-Dilinoleylcarbamoyloxy-3-dimethylaminopropane (DLin-C-DAP), 1,2-Dilinoleoyl-3-dimethylaminopropane (DLin-DAP), 1,2-Dilinoleyloxy-N,N-dimethylaminopropane (DLinDMA), 2,2-Dilinoleyl-4-dimethylaminomethyl-[1,3]-dioxolane (DLin-K-DMA), 2,2-dilinoleyl-4-(2-dimethylaminoethyl)-[1,3]-dioxolane (DLin-KC2-DMA), (6Z,9Z,28Z,31Z)-heptatriaconta-6,9,28,31-tetraen-19-yl 4-(dimethylamino)butanoate (DLin-MC3-DMA), 1,2-dioleoyl-3-dimethylammonium propane (DODAP), N,N-dimethyl-(2,3-dioleyloxy)propylamine (DODMA), dioctadecylamidoglycyl carboxyspermine (DOGS), Spermine cholesterylcarbamate (GL-67), bis-guanidinium-spermidine-cholesterol (BGTC), 3 β-(N(N',N'-dimethylaminoethane)-carbamoyl)cholesterol(DC-Chol), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), N-t-butyl-N'-tetradecylamino-propionamidine (diC14-amidine), Dimethyldioctadecylammoniumbromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride (DODAC), Dioleyloxypropyl-3-dimethyl hydroxyethyl ammonium bromide (DORIE), N-(1-(2,3-dioleyloxy)propyl)-N-2-(sperminecarboxamido)ethyl)-N,N-dimethylammonium trifluoracetate (DOSPA), 1,2-dioleoyltrimethyl ammonium propane chloride (DOTAP), N-(1-(2,3-dioleyloxy)propyl)-N,N,N-trimethylammonium chloride (DOTMA), ALC-0159 (α-[2-(ditetradecylamino)-2-oxoethyl]-ω-methoxy-poly(oxy-1,2-ethanediyl), Cas#1849616-42-7), cKK-E12 (3,6-bis[4-[bis(2-hydroxydodecyl)amino]butyl]-2,5-piperazinedione, CAS #1432494-65-9), ALC-0315 (2-hexyl-decanoic acid, 1,1'-[[(4-hydroxybutyl)imino]di-6,1-hexanediyl] ester, CAS# 2036272-55-4), 9A1P9 (2-(dioctylamino)ethyl nonyl hydrogen phosphate), SM-102 (8-[(2-hydroxyethyl)[6-oxo-6-(undecyloxy)hexyl]amino]-octanoic acid, 1-octylnonyl ester, CAS# 2089251-47-6), FTT5 (CAS# 2328129-27-5), L-319 (9-[4-(dimethylamino)-1-oxobutoxy]-heptadecanedioic acid, 1,17-di-(2Z)-2-nonen-1-yl ester, CAS# 1351586-50-9), 306Oi1 (tetrakis(8-methylnonyl) 3,3',3'',3'''-(((methylazanediyl)bis(propane-3,1-diyl))bis(azanetriyl))tetrapropionate, CAS# 2322290-93-5), or a combination thereof.

4. The nanoparticle of claim 1, wherein the structural lipid is 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), or a combination thereof.

5. The nanoparticle of claim 1, wherein the PEG lipid is a PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, or a combination thereof.

6. The nanoparticle of claim 1, wherein the PEG lipid is PEG-c-DOMG, PEG-DMG, PEG-DLPE, PEG-DMPE, PEG-DPPC, PEG-DSPE, or a combination thereof.

7. The nanoparticle of claim 6, wherein the PEG lipid comprises a PEG moiety of from 1000 daltons to 20,000 daltons.

8. The nanoparticle of claim 1, wherein:
   the ionizable lipid is DLin-MC3-DMA;
   the structural lipid is 1,2-distearoyl-sn-glycero-3-phosphocholine (DSPC);
   the PEG lipid is 1,2-dimyristoyl-rac-glycerol-methoxy (poly(ethylene glycol)-2000 (DMG-PEG$_{2K}$);
   or a combination thereof.

9. The nanoparticle of claim 1, wherein the nanoparticle has a nanoparticle size of from greater than zero to 500 nm.

10. The nanoparticle of claim 1, comprising:
    from 45 mol % to 55 mol % of the ionizable lipid;
    from 37 mol % to 40 mol % of the β-sitosterol;
    from 9 mol % to 10 mol % of the structural lipid; and
    from 3.5 mol % to 4.5 mol % of the PEG lipid;
    in amounts relative to each other.

11. The nanoparticle of claim 10, wherein:
    the ionizable lipid is DLin-MC3-DMA;
    the structural lipid is 1,2-distearoyl-sn-glycero-3-phosphocholine (DSPC); and
    the PEG lipid is 1,2-dimyristoyl-rac-glycerol-methoxy (poly(ethylene glycol)-2000 (DMG-PEG$_{2K}$).

12. An inhalable formulation, comprising a nucleic acid encapsulated within a nanoparticle, wherein the nanoparticle is a nanoparticle according to claim 1.

13. The inhalable formulation of claims 12, wherein the nucleic acid is an mRNA.

14. The inhalable formulation of claim 12, wherein the nanoparticle is a nanoparticle according to claim 10.

15. The inhalable formulation of claim 12, further comprising a carrier selected from a balanced salt solution or an isotonic saline.

16. A method, comprising administering by inhalation to a subject an inhalable formulation according to claim 12.

17. The method of claim 16, wherein administering the formulation comprises nebulizing the formulation and administering the nebulized formulation to the subject.

* * * * *